US008986711B2

(12) United States Patent
Larraga Rodriguez De Vera et al.

(10) Patent No.: US 8,986,711 B2
(45) Date of Patent: Mar. 24, 2015

(54) VACCINE TO PROTECT ANIMALS AGAINST LEISHMANIA

(75) Inventors: Vicente Emilio Larraga Rodriguez De Vera, Madrid (ES); Gloria Gonzalez Aseguinolaza, Madrid (ES); Maria Jesus Ramiro Ibanez, Madrid (ES); Juan Antonio Castillo Hernandez, Saragossa (ES); Javier Lucientes Curdi, Saragossa (ES)

(73) Assignees: Consejo Superior de Investigaciones Cientificas, Madrid (ES); Universidad de Zaragoza, Saragossa (ES); Laboratorios Hipra, S.A., Amer (ES)

( * ) Notice: Subject to any disclaimer, the term of this patent is extended or adjusted under 35 U.S.C. 154(b) by 0 days.

(21) Appl. No.: 10/468,618

(22) PCT Filed: Feb. 21, 2002

(86) PCT No.: PCT/ES02/00077
§ 371 (c)(1),
(2), (4) Date: Mar. 16, 2004

(87) PCT Pub. No.: WO02/066054
PCT Pub. Date: Aug. 29, 2002

(65) Prior Publication Data
US 2004/0156866 A1    Aug. 12, 2004

(30) Foreign Application Priority Data

Feb. 21, 2001  (ES) ........................................ 0100402
Sep. 12, 2001  (ES) ........................................ 0102057

(51) Int. Cl.
| | |
|---|---|
| *A61K 39/00* | (2006.01) |
| *A61K 49/00* | (2006.01) |
| *A61K 39/02* | (2006.01) |
| *C07K 14/44* | (2006.01) |
| *A61K 39/008* | (2006.01) |

(52) U.S. Cl.
CPC .............. *C07K 14/44* (2013.01); *A61K 39/008* (2013.01); *A61K 39/00* (2013.01); *A61K 2039/5256* (2013.01); *A61K 2039/53* (2013.01); *A61K 2039/55538* (2013.01); *A61K 2039/57* (2013.01); *C12N 2799/021* (2013.01)
USPC ............. 424/269.1; 61/9.1; 61/9.2; 61/184.1; 61/234.1

(58) Field of Classification Search
USPC ................. 424/184.1, 185.1, 234.1; 530/300; 536/23.1
See application file for complete search history.

(56) References Cited

PUBLICATIONS

Gonzalez-Aseguinolaza (FEBS, 259, 909-916, 1999).*
Afonso et al (Science, vol. 263, Jan. 14, 1994), 235-237.*
Dumonteil et al (Vaccine 21, 2003, p. 2161-2168).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second, 196-217 paragraph).*
Thomas E. Creighton, in his book, "Proteins: Structures and Molecular Properties, 1984", (pp. 314-315).*
Melby et al (Infection and Immunity, 2001, 69:4719-4725).*
Gonzalez-Aseguinolaza (Eur. J. Biochem., 259, 909-916, 1999, FEBS).*
Gonzalo et al (Microbes and Infection 3, 2001, p. 701-711).*
Paoletti et al (Proc. Natl. Acad. Sci. U.S.A, Vo. 93, p. 11349-11353).*
Afonso et al (Science, vol. 263, Jan. 14, 1994).*
Gonzalez-Aseguinolaza (Eur J Biochem. 259, 909-916 (1999)).*
Stobie (PNAS, Jul. 18, 2000, vol. 97, No. 15, p. 8427-8432).*
Paoletti (Proc. Natl. Acad. Sci. U.S.A, Vo. 93, p. 11349-11353).*
Gurunathan, et al., "Vaccination with DNA encoding the immunodominant LACK parasite antigen confers protective immunity to mice infected with lesihmania major". Oct. 1997. The Journal of Experimental Medicine. vol. 186 (7) pp. 1137-1147.
Gonzalez-Aseguinolaza, et al. "Molecular cloning, cell localization and binding affinity to DNA replication proteins of the p36/LACK protective antigen from leishmania infantum". 1999. Eur. J. Biochem. vol. 259, pp. 909-916.
Mattner, et al. "Interleukin—12 is indispensable for protective immunity against leishmania major". Nov. 1997 Infect. Immun. vol. 65 (11). pp. 4378-4383.
Raja Gabaglia, et al. "A single intramuscular injection with adenovirus expressing IL-12 protects BALB/c mice against leishmania major infection, while treatment with an IL-4-expressing vector increases disease susceptibility in b10.D2 mice". 1999 J. Immunol. vol. 162, pp. 753, 760.
Gonzalo, et al. "Protective immune response against cutaneous leishmaniasis by prime/booster immunization regimens with vaccinia virus recombinants expressing leishmania infantum p 36/LACK and IL-12 in combination with purified p36". Mar. 2001. Microbes and Infection, vol. 3, pp. 701-711.

* cited by examiner

*Primary Examiner* — Rodney P Swartz
(74) *Attorney, Agent, or Firm* — Tristan A. Fuierer; Moore & Van Allen, PLLC

(57) ABSTRACT

The present invention is generally related to the prevention of leishmaniasis in animals, particularly infection caused by *Leishmania* sp., based on the use of *Leishmania infantum* P36 protein or an immunogenic fragment of the latter, or involving an expression system for the mentioned protein or fragment—optionally in combination with a compound stimulating the production of a Th1-type cellular immune response—and comprising various vaccination protocols in application to *Leishmania* sp. based on the mentioned vaccine.

11 Claims, 7 Drawing Sheets

VACCINE TO PROTECT ANIMALS AGAINST LEISHMANIA

CROSS-REFERENCE TO RELATED APPLICATIONS

Figure 1:
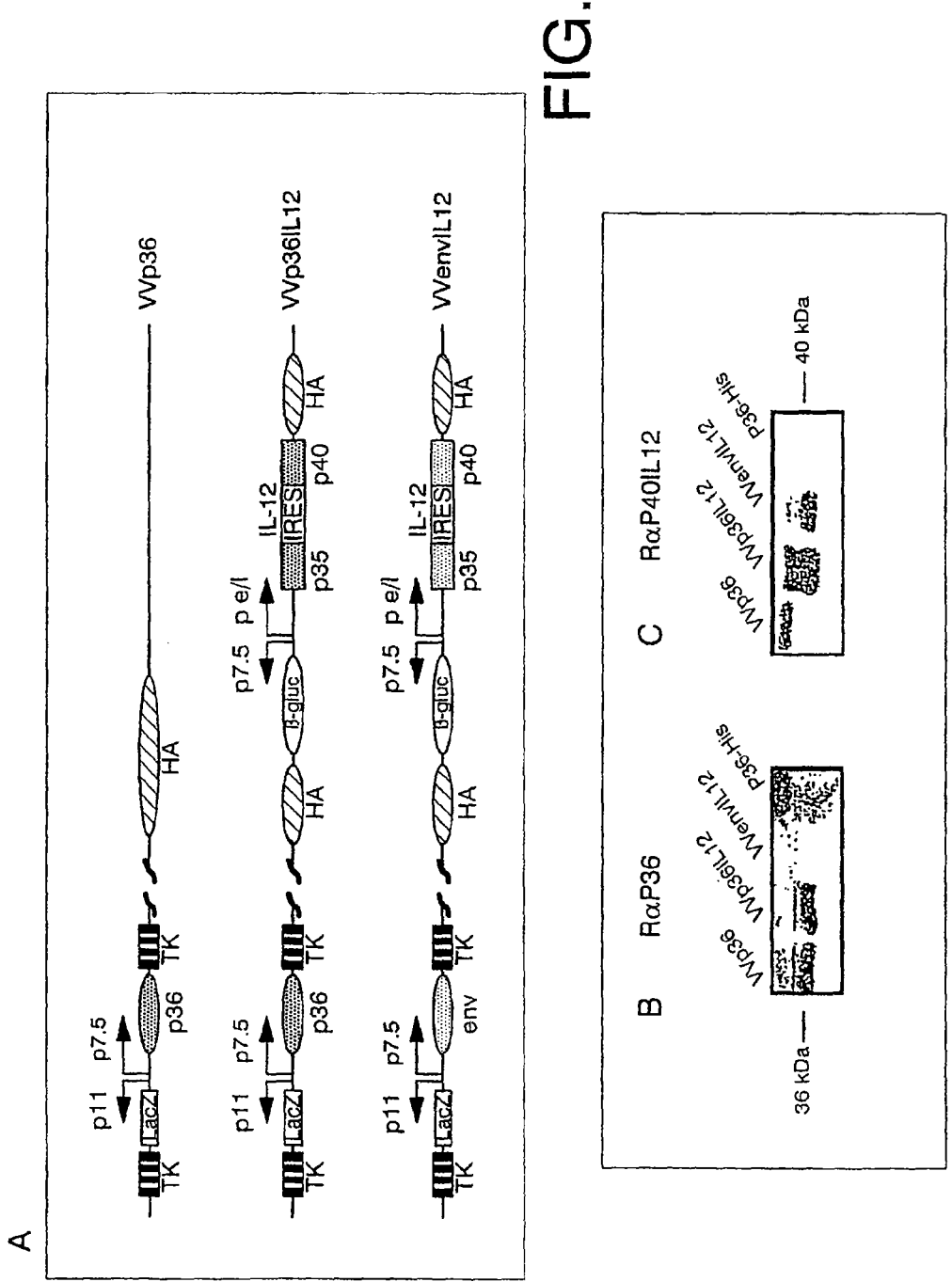

This application is filed under the provisions of 35 U.S.C. §371 and claims the priority of International Patent Application No. PCT/ES2002/00077, filed on 21 Feb. 2002 in the name of Consejo Superior de Investigaciones Científicas et al. and entitled "Vaccine to Protect Animals Against *Leishmania*," which in turn claims priority of Spanish Application Nos. P0102057 (España), filed 12 Sep. 2001 in the name of Consejo Superior de Investigaciones Científicas et al. and entitled "Addition to Patent ES200100402 Vaccine for Protecting Dogs from *Leishmania*," and P0100402 (España), filed on 21 Feb. 2001 in the name of Consejo Superior de Investigaciones Científicas et al. and entitled "Vaccine for Protecting Animals from *Leishmania*."

SECTOR OF THE TECHNIQUE

The invention is related, in general, with the prevention of leishmaniasis in animals, in particular, with a vaccine to protect against infection caused by *Leishmania* sp., based on a recombinant virus vaccine comprising a gene or a sequence of DNA that encodes for the associated antigen of *Leishmania* and a gene or a sequence of DNA that encodes for a molecule that stimulates the production of a Th1 type cellular immune response.

BACKGROUND TO THE INVENTION

Leishmaniasis comprises a group of parasitic illnesses caused by various species of the genus *Leishmania*. Depending on the immune response of the host, the infectious strain and the virulence of the parasite, the clinical manifestations vary from skin lesions that heal spontaneously, to the visceral (proving fatal if not treated) of the disease. The World Health Organization (WHO) has estimated that some 12 million people worldwide are infected and some 350 million people are at risk of infection (1). In Mediterranean countries the infection is zoonotic and the domestic dog is the main reservoir. The endemic strain of *Leishmania* in the Mediterranean area is *Leishmania infantum*, which infects both humans and dogs, producing skin and visceral leishmaniasis (2). Some epidemiological studies have indicated that in Spain approximately 7% of all dogs could be infected, whereas other authors have shown that 10-37% of dogs in the south of France developed visceral leishmaniasis (3). The WHO has estimated that between 2% and 9% of all patients with AIDS in southern Europe developed visceral leishmaniasis, since *L. infantum* is the cause of the third most frequent parasitic infection in HIV positive patients in the area mentioned (4).

An appropriate method of combating endemic leishmaniasis in Mediterranean countries and other parts of the world would be the creation of a vaccine able to confer long-term immunity against the parasite. Viability of a vaccine against this complex parasite has been suggested by the fact that the patients who recovered from the natural infection developed a strong immunity to *Leishmania* (5, 6).

As is well known, in mice, dogs and humans, clones of the $CD4^+$ T helper cells (adjuvant) can divide into two functional sub-series, Th1 y Th2, in accordance with the profile of the lymphokines produced. The sub-series Th1 preferentially produces gamma interferon (IFN-γ), whereas the sub-series Th2 produces predominantly the interleukin (IL) 4 [IL-4] (7-9).

In a mouse model infected with *Leishmania major* (the species that produces skin leishmaniasis), a clear correlation has been found between resistance to infection and the creation of a CD4+Th1 response and, on the other hand, the susceptibility and the development of CD4+Th2 responses (10, 11). Likewise, in humans and dogs resistance to visceral leishmaniasis is also associated with a Th1 response (12-15).

It has recently been shown that interleukin-12 (IL-12) is indispensable to provide protective immunity against *L. major*, as it initiates protective immune Th1 responses and regulates the proliferation of the subpopulation of T cells (16). It is in fact well established that IL-12 plays a critical role in the generation of Th1 cells and on the optimum differentiation of T cytotoxic lymphocytes (17). On the other hand IL-12 has also been used as a protective adjuvant in other models, such as *Schistosoma* (25), *Listeria* (26) or *Bordetella* (27).

In experimental vaccination tests against murine leishmaniasis, several antigens have been used, achieving different levels of protection. Among these are: gp63 of *L. major* (18), gp46 (19), LeIF (20, 21), LACK (22) genome libraries of expressing *L. major* (23). Likewise, the antigen gp46 of *L. amazonensis* expressed by a recombinant vaccine virus provides encouraging results with a high degree of protection and long-term immunological memory (24).

LACK is a protein of 36 kDa of *L. major*, so called for its homology with the protein RACK (receiver of activated kinase C in mammals) It has been demonstrated that a fragment of 24 kDa of this protein protects against exposure to *L. major* in mice when administered subcutaneously as a soluble protein in combination with the co-stimulating cytokine IL-12. Similarly, mice that received this antigen together with IL-12 showed a negative regulation in the number of IL-4 producing cells in the draining lymph nodes 6 weeks after infection with *L. major* and a positive regulation of the transcripts of IFN-γ in comparison with untreated mice (22). The mice became tolerant to LACK (transgenic mice that expressed the antigen in the thymus). Other studies have shown that the protective efficacy of soluble LACK of *L. major* together with IL-12 was similar to the efficacy obtained by immunisation with 100 μg of DNA that the same antigen expressed (28).

The protein P 36 of *L. infantum* has recently been cloned and characterised (29). Analysis of the aminoacid sequence of this protein has shown that P36 is well preserved (96-99%) among the strains studied of *Leishmania, L. major* and *L. chagasi* (22, 30).

The protective capacity of P36 of *L. infantum* has previously been tested in Balb/c mice immunised with this soluble protein or with an expressing system that expresses this protein in some discharge trials that comprised the administration to these animals of an initial dose and another booster dose of the antigen, followed by exposure to *L. major* promastigotes and it has been determined by the evaluation of the lesions in the pad of the paw where the parasite was inoculated, the parasitic load present in the lymph nodes and the immunological parameters before and after exposure to the parasite and which forms part of the purpose of this patent application PCT [Patent ES200100402, applied for on Feb. 21, 2001 entitled "VACUNA PARA LA PROTECCION DE ANIMALES FRENTE A *LEISHMANIA*"]. Subsequently, the same authors described for the first time positive results on the protection of the host animal par excellence of the illness, the dog, reservoir in Europe and South America and the type of cellular response against the illness by means of direct infection by *L. infantum* in dogs. (Patent ES200102057, applied for on 12 Sep. 2001, entitled "ADICION DE LA PATENTE ES200100402 VACUNA PARA LA PROTECCION DE PERROS FRENTE A *LEISHMANIA*) which is likewise included as part of this Patent application PCT.

DESCRIPTION OF THE INVENTION

BRIEF DESCRIPTION OF THE INVENTION

This patent is faced with the problem of providing vaccines and immunisation protocols capable of protecting animals, dogs among others, and humans from infection caused by *Leishmania infantum*, the causative agent of the canine infection and of visceral leishmaniosis in Europe.

The solution provided by this invention is based on the fact that the inventors have observed that the joint expression or not in an animal of genes that codify an associated antigen to leishmania, e.g., the antigen P36 of *L. infantum*, and a molecule that stimulates production of a Th1 type cellular immune response, for example, murine IL-12, contained in an rVV or in a plasmid pRSET-B able to infect said animal, induces a Th1 type cellular immune response which is co-related to protection against leishmaniasis.

An object of this invention is a vaccine to protect animals against infection caused by *Leishmania* sp. That comprises the protein P36 of *L. infantum*, or an immunogenic fraction thereof, together with, optionally, a compound able to stimulate the production of a Th1 type cellular immune response.

A further object of this invention is a vaccine that comprises an expression system of the protein P36 of *L. infantum* or an immunogenic fraction thereof, in which the said expression system comprises, at least, one DNA sequence that codifies the protein P36 of *L. infantum* or an immunogenic fraction thereof and, optionally, a DNA sequence that codifies a compound capable of stimulating the production of a Th1 type cellular immune response. Said expression system is also an additional objective of this invention.

Another additional objective of this invention is the use of the protein P36 of *L. infantum* or an immunogenic fraction thereof or the previously mentioned expression system in the elaboration of a vaccine for protection of animals from infection caused by *Leishmania* sp.

Another additional objective of this invention is the use of an expression system of the protein P36 of *Leishmania* sp. or an immunogenic fraction thereof and, optionally, of a compound able to stimulate the production of an immune response of the type Th1,for the elaboration of a vaccine to be administered as a booster dose in an immunisation protocol for animals, which comprises an initial immunisation with an immunogen of *Leishmania* sp., in soluble form, and a subsequent immunisation with a booster dose as a means of protecting animals from the infection caused by *Leishmania* sp.

A further additional objective of this invention is the use of the previously mentioned vaccines in immunisation protocols of animals, in particular dogs, against *L. infantum* that comprises at least an initial dose and a further booster dose of these vaccines in a series of combinations, among others, which are indicated below:

| Initial dose | Booster dose |
|---|---|
| Soluble P36 | Virus vaccine |
| Plasmid | Plasmid |
| Plasmid | Virus vaccine |

Where, the plasmid and the virus vaccine are expression systems comprising a DNA sequence that codifies the protein p36 of *L. infantum* or an immunogenic fraction thereof and also the vaccine comprises, optionally, a co-stimulating compound able to stimulate the production of a Th1 type cellular immune response.

DETAILED DESCRIPTION OF THE INVENTION

This addition provides a vaccine, of use in protecting animals from infection caused by *Leishmania infantum*, hereinafter the vaccine of the invention, which comprises a therapeutically effective quantity of:

1) an antigen chosen from between: protein P36 of *L. infantum* or of an immunogenic fraction thereof and, optionally, a co-stimulating compound able to stimulate the production of a Th1 type cellular immune response,
2) an expression system of the protein P36 of *L. infantum* or an immunogenic fraction thereof, which comprises a DNA sequence that codifies the protein P36 of *L. infantum* or an immunogenic fraction thereof and, optionally, a DNA sequence that codifies a co-stimulating compound able to stimulate the production of a Th1 type cellular immune response; and, optionally,
3) one or more adjuvants and/or pharmaceutically acceptable vehicles.

As it is used in this description, the term "animal" refers to vertebrate animals, including human beings. Likewise, in the sense used in this description, the expression "therapeutically effective quantity" refers to the quantity of protein P36 of *L. infantum* or of an immunogenic fraction thereof or an expression system of the protein P36 of *L. infantum* or of an immunogenic fraction thereof, calculated to produce the desired effect.

The cloning and characterisation of the protein P36 of *L. infantum* has been described by González-Aseguinolaza et al. (29).

In the sense used in this description, the expression "immunogenic fraction of the protein P36 of *L. infantum*" refers to any fragment of said protein that comprises, at least, 20%, preferentially, at least, 50% of the sequence of aminoacids of said protein P36 of *L. infantum* and which also conserves the biological activity of said protein, i.e. it is able to induce an immune response.

The vaccine of this patent may contain, if desired, a co-stimulating compound able to stimulate the production of a Th1 type cellular immune response. said co-stimulating compound could be any compound able to stimulate the production of a Th1 type cellular immune response, for example, an interleukin 12 (IL-12).

In the sense used in this description, the expression "able to stimulate the production of a Th1 type cellular immune response" includes any compound that stimulates the production of a cellular immune response in which the relation IFN-γ/IL-10 is greater than 1. The ability to produce a Th1 type cellular immune response can be determined in animals on the basis of the production of IFN-γ by the lymphocytes from the IFN-γ specific RNA of the dog by means of PCR using specific initiators and using arbitrary units of absorption against a control of non-immunised dog cells as well as an internal glyceraldehyde dehydrogenase control and a positive control on the basis of dog lymphocytes activated in a culture with phytohemiglutinenes (PHA). The same protocol, with necessary changes with respect to initiators, can be carried out to determine the production of IL-4 or IL-10 in the cellular immune response of the type Th2.

In a particular realisation, the vaccine of the invention comprises a therapeutically effective quantity of the protein P36 of *L. infantum* or of an immunogenic fraction thereof, together with, optionally, one or more adjuvants and/or pharmaceutically acceptable vehicles.

In another particular realisation, the vaccine of the invention comprises a therapeutically effective quantity of the protein P36 of *L. infantum* or of an immunogenic fraction thereof, one or more co-stimulating compounds able to stimulate the production of a Th1 type cellular immune response and, optionally, one or more adjuvants and/or pharmaceutically acceptable vehicles.

The vaccine of the invention may also contain an expression system of the protein P36 of *L. infantum* or an immunogenic fraction thereof, which comprises, at least, a DNA sequence that codifies the protein P36 of *L. infantum* or an immunogenic fraction thereof and, optionally, a DNA sequence that codifies a co-stimulating compound able to stimulate the production of a Th1 type cellular immune response.

The expression system of the protein P36 of *L. infantum* or of an immunogenic fraction thereof present in a type of vaccine of the invention may be any expression system able to express said protein or fragment functionally, i.e. able to induce an immune response in the immunised animal. In a particular realisation, said expression system is based on the virus Vaccinia (VV), which has the advantage of being an expression system of antigens that can produce an immune response of the type Th1. The VV is a cytoplasmic DNA virus belonging to the poxvirus family, which provides a simple, safe and cheap vaccination protocol. The VV is a powerful vector satisfactorily used as a live vaccine to eradicate smallpox (31). Several recombinant VV (rVV) have been described that express different genes that can induce long-term immunologic effects that can lead to protection against exposure to a pathogen in numerous experimental models (32-34). Also rVV has been used as an efficacious and safe oral vaccine against rabies, able to confer protection on wild animals, such as the red fox in Europe and the skunk in the United States (35). On the other hand, it has been described how mice, immunised with rVV that co-express the protein env of HIV-1 and IL-12 give rise to a notable increase CD8$^+$ T cells producing specific IFN-γ for env (37). The safety of VV is guaranteed by using the Ankara strain of modified VV (MVA), which lacks the genes that neutralise the immune system and induces protection against pathogens in animal model systems (36).

In a particular realisation, the expression system of the protein P36 of *L. infantum* or of an immunogenic fraction thereof present in a type of vaccine of the invention, only includes the sequence or sequences of DNA that codify the o protein P36 of *L. infantum* or an immunological fraction thereof. In another particular realisation, said expression system of the protein P36of *L. infantum* or of an immunogenic system thereof, present in a type of vaccine of the invention includes, at least, a DNA sequence that codifies the protein P36 of *L. infantum* or an immunogenic fraction thereof and, at least, a DNA sequence that codifies the co-stimulating compound able to stimulate the production of a Th1 type cellular immune response.

The sequence or sequences of DNA that codify the protein P36 of *L. infantum* or a fragment thereof, as well as the sequence or sequences of DNA that codify one or more co-stimulating compounds able to stimulate the production of a Th1 type cellular immune response, can be, in a particular realisation, operationally linked to a transcription regulatory region.

In the sense used in this description, the expression "transcription regulatory region" includes all the necessary elements for transcription and can include the necessary elements for the specific regulation and transcription the cell. Therefore, transcription regulatory region includes, at least, a promoter and can include, optionally, other regulating sequences, such as potentiators and union sites of the transcription factor.

As it is used in this description the expression "operationally linked" refers to a juxtaposition in which the implicated components are located in such a way that they can function in the manner described, for example as a promoter it is operationally linked to a codifying sequence if the promoter affects its transcription or expression.

The transcription regulatory region to which they are operationally linked to the DNA sequence that codifies the protein P36 of *L. infantum* and the DNA sequence that codifies said co-stimulating compound can be any known regulatory region, for example, a regulatory region of a VV gene. He DNA sequence that codifies the protein P36 of *L. infantum* and the DNA sequence that codifies said co-stimulating compound may be operationally linked to the same transcription regulatory sequence or, alternatively, they may be operationally linked to different transcription regulatory sequences.

The expression system of the protein P36 of *L. infantum* of this invention can be obtained by conventional techniques of handling nucleic acids described in any manual of molecular cloning known by the experts in this field. In a particular realisation, said expression system is an rVV called VVp36IL12, which simultaneously expresses the antigen P36 of *L. infantum* and the sub-units P35 and P40 of the murine IL-12 and whose construction is described in example 1. The joint expression of the protein P36 of *L. infantum* and of the co-stimulating compound confers, at least, partial immunity against *Leishmania*. In the sense used in this description, the expression "immunity" refers to a reduction and/or a prevention of one or more symptoms associated with the infection caused by *Leishmania* sp.

The adjuvants and pharmaceutically acceptable vehicles that can be used in the vaccine of the invention are the adjuvants and vehicles known to technicians in the material and habitually used in the formulation of vaccines. In a particular realisation, said vaccine is prepared in the form of an aqueous solution or suspension in a pharmaceutically acceptable solvent, such as saline solution, phosphate buffered saline solution (PBS), or any other pharmaceutically acceptable diluent.

The vaccine of the invention may administered by any appropriate administration route that has the result of a protective response to leishmaniasis, for which reason said vaccine will be formulated in a pharmaceutically appropriate manner for the chosen administration route. In a particular realisation administration of the vaccine provided by this invention is effected parenterally, for example intraperitoneally, subcutaneously etc.

In another aspect, the invention refers to the use of the protein P36 of *L. infantum* or an immunogenic fraction thereof, in the elaboration of a vaccine to protect animals, dogs in particular, from infection caused by *Leishmania* sp.

Likewise, the invention also refers to the use of he expression system of the protein P36 of *L. infantum* or of an immunogenic fraction thereof mentioned previously, which comprises a DNA sequence that codifies the protein P36 of *L. infantum* or an immunogenic fraction thereof and, optionally, a DNA sequence that codifies a co-stimulating compound able to stimulate the production of a Th1 type cellular immune response, in the elaboration of a vaccine for protecting animals, dogs in particular, from infection caused by *Leishmania* sp.

This invention also contemplates an animal immunisation protocol, of dogs in particular, from *Leishmania* sp. that comprises administering to said animal, a dog in particular, a vaccine provided by this invention, either alone or in combination with another immunogen of *Leishmania* sp. able to produce an immune response, either from a single dose or by means of an initial dose and one or more booster doses with said vaccine or said immunogen of *Leishmania*.

Therefore, this invention also refers to the use of an expression system of the protein P36 of *L. infantum* or of an immunogenic fraction thereof in the elaboration of a vaccine to be administered as:

a) a booster dose in the immunisation protocol of animals, comprising an initial immunisation with an immunogen of *Leishmania* sp., in a soluble form and a subsequent immunisation with a booster dose or b) An initial dose or booster dose in an immunisation protocol for animals, dogs among others, that comprises an initial immunisation with an expressing system of the protein P36 of *L. infantum* and subsequent immunisation with a booster dose that comprises an expression system of the protein P36 of *L. infantum* or of an immunogenic fraction thereof, which, optionally, comprises also one or more DNA sequences that codify a co stimulating compound able to stimulate the production of a Th1 type cellular immune response, as a means of protecting animals from infection caused by *Leishmania* sp.

In a particular realisation, the immunogen of *Leishmania* sp. used in the initial immunisation is a protein P36 of *L. infantum* or an immunogenic fraction thereof and the booster dose comprises an expression system of the protein P36 of *L. infantum* or of an immunogenic fraction thereof, which, optionally, also comprises one or more sequences of DNA that codify a co-stimulating compound able to stimulate the production of a Th1 type cellular immune response.

Different immunisation protocols have been tested with the intention of obtaining a Th1 immune response that leads to protection from *Leishmania*. For this, in the first place, rVV were generated that co-expressed the antigen P36 of *L. infantum* and the cytokine IL-12 (VVp36IL12) (Example 1) and they were tested in Balb/c mice immunised with rVV by means of different immunisation protocols an exposure (discharge) to promastigotes of *L. major* (Example 2), measuring the conferred protection correlations by means of the measurement of the lesions in the cushion of the paw where the parasite had been administered, the parasitic load present in the lymph nodes are some immunological parameters (secretion of IFN-γ and IL-10; specific isotopes of IgG) before and after exposure to the parasite, obtaining elevated protection in the animals vaccinated with VVp36IL12.

A comparison of the different immunisation protocols tested allowed it to be established that initiation with the protein P36 of *L. infantum* soluble, followed by a booster with VVp36IL12 constitutes an optimum immunisation protocol, since it causes a reduction in the size of the lesions of approximately 52% and a reduction in the parasite load of more than 99% in infected animals (Example 2). This protection is correlated with the activation of a type of Th1 immune response, determined by the relationship of specific Ig2a/IgG1 and IFN-γ/IL-10 (Example 3). These protocols are interesting in prophylaxis against species of *Leishmania* and, perhaps, other parasitic illnesses.

On the other hand, a second immunisation protocol was tested in such a way that the dogs were immunised with the gene P36 of *L. infantum* in a pRSET-B plasmid in two doses separated in time or in the plasmid in the first dose and with a second dose in VVp36, measuring the production of IL 4 interleukin and IFN gamma as well as the production of specific anti p36 antibodies in the dogs as well as their subtype IgG1 and IgG2 with the object of determining the type of response Th1 or Th2 that it induced in the animals.

The type of response seems to be, from the results obtained (Example 5 and Table 3), that it is of Th1 type in the dogs that has shown protection and of TH2 type in the positive controls (unwell).

These protocols are interesting in prophylaxis against species of *Leishmania* and, perhaps, other parasitic illnesses and they form part of this invention.

In another aspect, the invention also provides an expression system for the protein P36 of *L. infantum* or of an immunogenic fragment thereof, which comprises a DNA sequence that codifies the protein P36 of *L. infantum* or an immunogenic fraction thereof and, optionally, a DNA sequence that codifies a co-stimulating compound able to stimulate production of a Th1 type cellular immune response, on the condition that said expression system is not *Escherichia coli* if it comprises only the said DNA sequence that codifies the protein P36 of *L. infantum* or an immunogenic fragment thereof.

In a particular realisation, the expression system of the protein P36 of *L. infantum* or of an immunogenic fraction thereof, comprised a DNA sequence that codified the protein P36 of *L. infantum* or an immunogenic fraction thereof, in the case of which, the said expression is not *E. coli*. In another particular realisation, said expression system of the protein P36 of *L. infantum* or of an immunogenic fraction thereof comprises, at least, a DNA sequence that codified the protein P36 of *L. infantum* or an immunogenic fraction thereof and, at least, a DNA sequence that codifies a co-stimulating compound able to stimulate the production of a Th1 type cellular immune response, for example, an IL12.

The sequence or sequences of DNA that codify the protein P36 of *L. infantum* or a fragment thereof, as well as the AND sequence or sequences that codify one or more co-stimulating compounds able to stimulate the production of a Th1 type cellular immune response, can be, in a particular study, operationally linked to a transcription regulatory region. The transcription regulatory region to which they are operationally linked the DNA sequence that codifies the protein P36 of *L. infantum* and the DNA sequence that codifies said co-stimulating compound may be any known regulatory region, for example, a regulatory region of a gene of VV. The DNA sequence that codifies the protein P36 of *L. infantum* and the DNA sequence that codifies said co-stimulating compound may be operationally linked in the same regulatory sequence of the transcription or, alternatively, they may be operationally linked to regulatory sequences of different transcription.

The expression system of the protein P36 of *L. infantum* or of an immunogenic fraction thereof may be any expression system able to express said protein or fragment of functional form, i.e. able to induce an immune response in an immunised animal. In a particular realisation, said expression system is based, on the one hand on the VV and on the other in the plasmid pCI-neo (Promega).

The expression system of the protein P36 of *L. infantum* or of a fragment thereof, provided by this invention may be obtained by conventional handling techniques of nucleic acids described in any molecular cloning manual known to the experts in this material.

In the sense used in this description, the expression "induce an immune response" refers to a reduction and/or prevention of one or more symptoms associated with the infection caused by Leishmania sp.

In conclusion, the P36 of L. infantum and an expression system of it and the immunisation protocol of the invention that comprises the use of said protein or expression system causes an immune response of the type Th1 in dogs, which produces protection from leishmaniasis. This protocol, together with other antigens of *Leishmania*, could have greater application for controlling this and other parasitic illnesses. The use of very attenuated VV, e.g., MVA, will ensure safety in human beings.

BRIEF DESCRIPTION OF THE FIGURES

FIG. 1.—The generation and characterisation of rVV that express P36 of *L. infantum* by means of a Western analysis of protein expression. FIG. 1A is a schematic representation of the genomes of the different rVV generated, identified as VVp36, VVp36IL12 and VVenvIL12 (see the chapter relating to virus and cells in the Materials and Methods section). The gene that codifies the protein P36 de *L. infantum* (p36) was inserted in the locum of the thymidine kinase (TK) of the VV genome. Recombinant doubles of VV were generated by the insertion of the cassette that the genes contained that codified for murine IL-12 (p35 y p40) in the locum of the haemaglutinine (HA). Lac-Z and β-gluc are the selective markers, whereas p11, p7.5 and pe/l are different promoters of VV. FIGS. 1B and 1C show the result of the Western analysis of recombinant protein expression P36 and P40 (Example 1.4) using polyclonal rabbit antibodies anti-P36 (RαP36) of *L. infantum* (FIG. 1B) or monoclonal antibodies against the sub-unit P40 of IL-12 (RαP40IL12) murine (FIG. 1C).

FIG. 2.—Protection trial against *Leishmania* of mice immunised with VVp36 in comparison with soluble p36 and IL-12 (see example 2 test 1). FIG. 2A is a bar chart that shows the lesion size of each immunisation group infected with *L. major* at week 7 after exposure to the parasite. Each bar represents the mean value of the size of the lesion in the infected hind leg in comparison with the non-infected hind leg of each immunisation group (n=4) with SE. The groups marked with an asterisk (*) showed a significant reduction ($p<0.01$) in the size of the lesion at week 7 after exposure compared with the control group (PBS). The percentage reduction in the lesion compared with the control group (PBS) is shown between parentheses. FIG. 1B is a bar chart showing the parasite loads detected in each immunisation group 7 weeks after exposure to the parasite, in accordance with the protocol described in the Materials and Methods section. The bars represent mean values of samples of 4 animals±SD of 2 different determinations.

FIG. 3.—Combination of rVV that co-express P36 and IL-12 followed by administration of soluble P36 induces a high protection in mice infected with *L. major* (see Example 2 Test II). FIG. 3A is a bar chart showing the mean values of the lesion in the $7^{th}$ week after exposure to the parasite in the infected hind leg in comparison with the non-infected hind leg for the immunisation group (n=6) with SE. The groups marked with an asterisk (*) show a significant reduction ($p<0.01$) in the size of the lesion in the $7^{th}$ week after exposure compared with a control group (PBS). The reduction percentages of the lesion in comparison with the control group are shown in parentheses. FIG. 3B is a bar chart showing the parasite loads detected in each immunisation group 7 weeks after exposure, in accordance with the protocol described in the Materials and Methods section.

The bars represent mean values of samples of 4 animals ±SAD of 2 different determinations.

FIG. 4.—optimum protection test against *Leishmania* in mice that received an initial dose of P36 and were boosted with rVV that co expressed the antigen P36 and the cytokine IL-12 (see Example 2 Test III). FIG. 4A is a bar chart showing the size of the lesion in each immunisation group infected with *L. major* at week 7 after exposure to the parasite. Each bar represents the mean values of the size of the lesion in the infected hind leg in comparison with the non-infected hind leg of each immunisation group (n=8) with SE. The groups marked with an asterisk (*) showed a significant reduction ($p<0.01$) in the size of the lesion in the $7^{th}$ week after exposure in comparison with the control group (VVenvIL12), whereas the groups marked with 2 asterisks () showed a high and significant reduction ($p<0.05$) in the size of the lesion in the $7^{th}$ week after exposure in comparison with the control group. The reduction percentages of the lesion in comparison with the control group (VVenvIL12) are shown in parenthesis. FIG. 4**B is a bar chart showing the parasite loads detected in each immunisation group 7 weeks after exposure, in accordance with the protocol described in the Materials and Methods section. The bars represent mean values of 4 animals±SD of 2 different determinations.

FIG. 5.—immunisation with soluble P36 plus VVp36IL12 provides a greater protection than soluble P36 plus VVp36 in mice infected with *L. major* (see Example 2, Test IV). FIG. 5A is a bar chart showing the size of the lesion of each immunisation group infected with *L. major* at week 7 after exposure to the parasite. Each bar represents the mean values of the size of the lesion in the infected hind leg in comparison with the non-infected hind leg of each immunisation group (n=8) with SE. The groups marked with an asterisk (*) showed a significant reduction ($p<0.01$) in the size of the lesion the $7^{th}$ week after exposure in comparison with a control group (VVenvIL12). The reduction percentages of the lesion in comparison with the control group (VVenvIL12) are shown in parentheses. FIG. 5B is a bar chart that shows the parasite loads detected in each immunisation group 7 weeks after exposure, in accordance with the protocol in the Materials and Methods section. The bars represent the mean values of 4 animals±SD of 2 different determinations.

FIG. 6.—Production of IL 4 and IFNγ by the peripheral blood cells. This figure shows the production of mRNA corresponding to IL 4 and IFN-γ in the peripheral cells extracted from the animals of different groups throughout the immunisation experiment. Inoculation of the infection is marked as day zero. The measurement is in arbitrary absorption units having previously subtracted that corresponding to the internal control of glyceraldehydes dehydrogenase that is expressed in a constant way in cells. Each value is the mean of 5 determinations carried out in duplicate.

FIG. 7.—Determination of specific anti p36/lack antibodies in the serum of the dogs. This figure describes the production of specific ant p36/LACK antibodies in the different groups of dogs by means of ELISA the IgG2/IgG1 relation. Each value represents the mean of five dogs. The experiments in this case were carried out in triplicate and are expressed in A.UA. at 450 nm.

EXAMPLES OF THE INVENTION

The following Examples illustrate the invention and must not be considered as limiting its scope. In the Materials and Methods section, the virus, cells, mice, dogs parasites and reagents used in these Examples are identified as well as the methods for evaluating the parasite load, the response to specific antibodies to P36 of *L. infantum*, the production of cytokines and statistical analysis. In the Discussion section the results obtained are commented and discussed and the significance of these.

MATERIALS AND METHODS

Virus and Cells

The recombinants of vaccinia virus (rVV) used proceeded from the wild type Western Reserve strain (WR). In Example 1 the construction of the rVV called VVp36 (that expresses the antigen P36 of *L. infantum*) is described.

Green African monkey kidney cells and HeLa cells were cultivated in Eagle, modified by Dulbecco. Media supplemented with 10% of newborn calf serum [NCS] (obtained from Gibco BRL, Paisley, United Kingdom). All the virus were cultivated in HeLa cells and evaluated in BSC-40 cells.

Mice

Balb/c female mice were obtained from the Animal Service of the Centro Nacional de Biotecnología (Madrid, Spain) and were kept under pathogen free conditions. The mice were used when they were between six and eight weeks old.

Dogs

The protection experiments were carried out on female beagle dogs of 13 kg weight and 2 years of age and free from infection. The dogs were maintained in kennels for a period of 20 months (eighteen months after experimental infection) in an area protected from possible natural infections, which met the requirements of "Good laboratory practice" required by the EU. The group P+V was separated from the rest as it was treated with a virus, albeit attenuated. The animal room had windows protected by metallic mesh' which was treated fortnightly with a solution containing active insecticide against mosquitoes. Also there was a mosquito net on the door so as to avoid the possibility of there being dogs affected by natural infection. The four groups of dogs were inoculated two week after vaccination of the corresponding groups (PIP and PAVE) with $10^8$ parasites endovenously (day 0 of the experiment).

Parasites

*L. major* (WHOM/IR/-173) was donated by Dr. Nicholas Glaichenhaus (CNRS, Valbonne, France). The promastigotes were cultivated at 27.degree. C. in Schneider's medium (obtained from Gibco BRL, Paisley, United kingdom) supplemented with a 20% of foetal calf serum (FCS).

*L. infantum* (MHOM/FR/78/LEM-75) was obtained by Drs. Castillo and Lucientes (Faculty de Veterinary Science, Universdad de Zaragoza) from examples of naturally infected dogs. The identification of the strain of the parasite was performed on the Service of Parasitology of Majadahonda, I.S. Carlos III.

Reagents

The recombinant protein P36 of *L. infantum* was purified from bacteria, as has been previously described (29).

The soluble antigen of *Leishmania* (LSA) was prepared from promastigotes of *L. major* in stationary phase. Summarising, $2 \times 10^8$ promastigotes/ml were collected and resuspended in 10 ml of PBS. After three freezing/thawing cycles, the suspension was centrifuged 8,000×g and the supernatant liquid was collected in aliquots of 1 ml. The protein concentrations were estimated by the BCA method (Pierce, Rockford, Ill.).

Evaluation of the Parasite Load

The number of parasites present in the infected draining lymph nodes was quantified using the method of limiting dilution (43). Briefly, each group of poplitea lymph nodes, prior to homogenisation, was weighed and then diluted on a series of micro evaluation plates with a flat bottom and containing 96 wells that contained Schneider's medium supplemented with 20% of FRCS. The number of viable parasites per mg of tissue was determined from the greatest dilution from which the promastigotes could develop after 7 days' incubation at 27° C.

The number of parasites present in the infected draining lymph nodes was detected using the PCR detection method: Using the same method, the interleukin IL 4 and IFN gamma levels were evaluated to detect the activation state of the CD4+ cells and the most dominant sub-population (see below).

Measurement Specific Antibody Response Against *L. infantum*

Samples of serum were obtained, grouped before and after exposure to the parasite and they were analysed for the presence of specific P36 atibodies using an ELISA technique. Briefly, 96 Maxisorb plates (Nunc) were covered with recombinant P36 (3 µg/ml) for one night at 4° C. in PBS at pH 7.5. The plates were washed with PBS-Tween-20 at 0.05% (PBS-T) and blocked with BSA at 1% in PBS-T (blocking buffer) for at least an hour at 37° C. The serum samples were diluted in blocking buffer at 1:100, 1:500, 1:1.000 and 1:5.000 respectively, they were added in quantities of 50 µl/well and incubated for 1 hour at 37° C. Afterwards, the plates were washed three times. IgG, IgG1 or IgG2a goat anti-mouse conjugated with peroxidase (Southern Biotechnology Associates, Birmingham, Ala.) was added for 1 hour at 37° C. Subsequently, the plates were made to react with the peroxidase substrate OPD (Sigma, St. Louis, Mo.) and the absorbance measured at 492 nm in a Labsystem Multiskan Plus plate reader (Chicago, Ill.). The data obtained for the total specific anti-P36 IgG are not shown. Similar ELISA tests were performed using antigens rVV and LSA before and after exposure to confirm correct immunisation and the development of the humoral immune response of the mice (applicable to examples 1, 2 and 3).

On the other hand and applicable to examples 4 and 5, in brief, 96 Maxisorb plates (Nunc) were covered with recombinant P36 (4 µg/ml) for one night at 4° C. in carbonate buffer at pH 9.6. The plates were washed with PBS Tween-20 at 0.05% (PBS-T) and were blocked with BSA 1% in PBS-T (blocking buffer) for at least 1 hour at 37° C. the serum samples were diluted in blocking buffer 1:80 and incubated for 1 hour at 37° C. Afterwards, the plates were washed three times. Peroxidase conjugated IgG1 or IgG2 goat and bee antidog respectively were added (Bethyl Laboratories Inc. Tex., USA) for 1 hour at 37° C. (dil 1:500 and 1:3000 respectively). Subsequently the plates were made to react with the OPD peroxidase substrates (Sigma, St. Louis, Mo.) and the absorbance measured at 450 nm in a Fluostar Galaxy© plate reader 2000 BMG Labtechnologies (USA).

Evaluation of Cytokine Production

Cytokine levels of the supernatant liquid of the cell culture were determined by ELISA. At various times (immediately before exposure and 7 weeks after exposure) the mice were killed and the spleens and the draining lymph nodes were removed. Individual cellular preparations of these organs were cultivated in triplicate, at a density of 4×10$^6$ (cells/ml. Whole soluble P36 protein was added at 2 µg/ml, 1 µg/ml of LPS (Sigma, St. Louis, Mo.) (positive control) or PRIM alone (background control) in a final volume of 1 ml/well. The supernatant liquid was collected at 24, 48 and 72 hours and stored at −80° C. until use. Measurements of IFN-γ and IL-4 were evaluated by a specific ELISA using capture and secondary antibodies of Genzyme and following the manufacturer's instructions. The lower limit of detection of IFN-γ and IL-4 was 5 pg/ml and 15 pg/ml, respectively (applicable to examples 1, 2 and 3).

On the other hand and applicable to examples 4 and 5, the cytokine levels were determined using the measurement of specific RNA proceeding from peripheral cells (PUBIC) corresponding to each of those amplified by means of PCR. At varying times (immediately before exposure and fortnightly for 76 weeks after infection), peripheral cells (PMBC) were extracted with Trizol to obtain the corresponding RNA that was subsequently measured by PCR. In all cases an internal control was carried out with phosphoglyceraldehyde dehydrogenase that is expressed in a constant manner in the cells.

Obtaining the Antigen for the Direct Agglutination Test (DAT)

1.1. Organism:

Leishmania infantum (MHOM/FR/78/LEM-75). Strain ceded by Dr. Jorge Alvar of the Centro Nacional de Microbiologia, Instituto de Salud Carlos III, Majadahonda, Madrid.

1.2. Methodology for Elaborating the Antigen for the Direct Agglutination Technique:

1.—the promastigotes were cultivated at 26° C. in an RPMI 1640 medium, to which was added with penicillin-streptomycin (100 IU/mL and 104 µg/mL respectively) and foetal bovine serum at 10%(v/v) deactivated by heat. The medium thus prepared was sterilised by filtration through 0.22 µm pore membranes with between three and five days' growth, they were harvested by centrifugation at 4000 G for 10 minutes at 4° C.

2.—Five washings were performed with cold Locke solution at 3200 g for 10 minutes at 40° C.

3.—The artificial digestion was carried out by the addition of (0.4% w/v of trypsin 1:250 of Difco) in cold Locke solution and with a pH of 7.7.

4.—The relation of promastigotes and trypsin was 1/20.

5.—The promastigotes and trypsin were mixed and incubated at 37° C. for 45 minutes.

6.—Subsequently, the suspension was centrifuged five times with cold Locke solution at 3200G for 10 minutes.

7.—The cells were then counted and suspended at a concentration of 2×16 cells/mL.

8.—Once the cell numbers had been adjusted, an equal volume of formaldehyde dissolved in cold Locke solution was added and left to rest all night.

9.—To remove the remains of formaldehyde, it was centrifuged at 3200G for 10 minutes at 4° C. With Saline Citrate Solution and resuspended at the same concentration of (8).

10.—Coomassie blue was added at a final-concentration of 0.1% (w/v) and left under moderate stirring for 90 minutes.

11.—The remains of the dye were washed by centrifuging at 3200G for 10 minutes and the precipitate was washed twice in a Saline Citrate solution.

12.—The 0.4% formaldehyde solution was resuspended in Saline Citrate solution at the same concentration as (10).

13.—The antigen was stored under refrigeration at 40 C protected from light (see appendix 1).

1.3. Development of the DAT Technique:

1.—Microtitre plates were used of 12 by 8 wells and with a "V" shaped bottom.

2.—The sera were diluted in duplicate, starting from 1/100, for which

3.—50 µl of the diluent solution were added to each well except the second well.

4.—In the second well were added 100 µl of the 1/100 dilution of the problem serum.

5.—50 µl of the second well were added to the third, well mixed and 50 µl were passed from the third to the fourth. This process was repeated across all the plate and the last 50 µl of the twelfth well were discarded.

6.—The positive and negative control sera were placed in separate wells.

7.—The antigen was shaken to resuspend the cells and subsequently 50 µl of this were taken and added to each well.

8.—The plates were covered and shaken for 60 seconds clockwise and counter clockwise and left to incubate overnight in a horizontal position, taking care to leave them in a stable position and with no possibility of movement and protected from the light and drying.

1.4. Interpretation of the Results:

They were read against a white background. The positive result is that in which the viewed cell shows a uniform colour with no appreciable precipitation in the centre. All wells with antigen precipitations different to the negative control are considered positive. The results were read by two persons and the results compared.

1.5.—Bibliography

Boelaert, M., El Safi, S., Goetghebeur, E., Gomes-Pereira, S., Le Ray, D. y P. Van der Stuyft. 1999a. Latent class analysis permits unbiased estimates of the validity of DAT for the diagnosis of visceral leishmaniasis. *Tropical Medicine and international Health* 4(5):395401.

Boelaert, M., El Safi, M. Musa., Githure, J., Mbati, P., Gurubacharya, V. L., Shrestha, J., Jacquet, D., De Muynck, A., Le Ray, D y P. Van der Stuyft. 1999. Multi-centre evaluation of repeatability and reproducibility of the direct agglutination test for visceral leihmaniasis. *Tropical Medicine and international Health.* 4(1):31-37.

Boelaert, M., El Safi, S., Jacquet, D., De Muynck., Van der Stuyft, P. y D. Le Ray. 1999b Operational Validation of The Direct agglutination Test for Diagnosis of Visceral Leishmaniosis. *The American Journal of Tropical Medicine and Hygiene.* 60(1) 129-134.

De Korte, P. M., Harith, A. E., Dereure, J., Huigen, E., Faucherre, V. & van der Kaay, H. J. 1990.Introduction of an improved direct agglutination test for the detection of *Leishmania infantum* infection in southern France. *Parasitology Research,* 76: 526-530.

Harith, A. E., Kolk, A. H. J., Kager, P. A., Leeuwenburg, J., Muigai, R., Kiugu, S., Kiugu, S. y J. J. Laarman. 1986. A simple and economical direct agglutination test for serodiagnosis and seroepidemiological studies of visceral leishmaniasis. *Transactions of the Royal Society Medicine and Hygiene* 80, 583-587.

Harith, A. E., Kolk, A. H. J., Kager, P. A., Leeuwenburg, J., Faber, F. J., Muigai, R., Kiugu, S. y J. J. Laarman. 1987. Evaluation of a newly developed direct agglutination test (DAT) for serodiagnosis and ser-epidemiological studies of visceral leishmaniasis: comparison with IFAT and ELISA. *Transactions of the Royal Society Medicine and Hygiene.* 81.603606.

Harith, A. E., Slappendel, R. J., Reiter, I., van Knapen, F., de Korte, P., Huigen, E. y A. H. J. Kolk 1989. Application of a direct agglutination test for the detection of specific anti-Leishmania antibodies in the canine reservoir. *Journal of Clinical Microbiology.* 27:2252-2257.

Oskam, L., Nieuwenhuijs, J. L. y A. Hailu. 1999.Evaluation of the direct agglutination test (DAT) using freeze-dried antigen for the detection of anti leishmania antibodies in stored sera from various patient groups in Ethiopia *Transactions of the Royal Society of Tropical Medicine and Hygiene,* 93,275-277.

Slappendel, R and E. Teseke. A revew of canine leishmaniasis presenting outside endemic areas. 1999. Canine Leishmaniasis an update. Proceding of International Canine Leishmaniasis Forum. Barcelona, Spain. pp. 54-59.

Appendix I.—Reagents and Solutions for the Preparation of the Antigen Used in the Direct Agglutination Technique a).—Reagents:
  Sodium chloride (NaCl)
  Potassium chloride (KCl)
  Calcium chloride ($CaCl_2$)
  Sodium hydrogen carbonate ($NaHCO_3$)
  Tri-sodium citrate
  Gelatine (Difco, USA)
  Trypsin (1:250 Difco, USA)
  B-mercaptoethanol
  Brilliant Coomassie blue (R 250, Merck)
  Formaldehyde 38%
  Bovine foetal serum (obtained from Gibco BRL, Scotland)
  RPMI 1640 medium (obtained from Gibco BRL, Scotland)
  Penicillin-streptomycin (obtained from Gibco BRL, Scotland)
  Gentamycin (Schering-Plough, España)

| B.1. - Saline phosphate buffer solution (PBS), pH 7.2. | |
| --- | --- |
| Sodium chloride (NaCl) | 8 gm |
| Monopotassium phosphate ($KH_2PO_4$) | 0.2 gm |
| Disodium phosphate ($Na_2HPO_4 \cdot 12H_2 0$) | 2.88 gm |
| Potassium chloride (KCl) | 0.2 gm |
| Distilled water (q.s.f) | 1000 Ml |
| B.2. - Physiological saline serum | |
| Sodium chloride (NaCl) | 8.9 gm |
| Distilled water (q.s.f) | 1000 mL |
| B.3. - Locke solution: | |
| D-Glucose | 0.25% (p/v) |
| Sodium chloride | 0.9% (p/v) |
| Potassium chloride | 0.04% (p/v) |
| Calcium chloride | 0.02% (p/v) |
| Sodium hydrogen carbonate | 0.02% (p/V) |
| Distilled water (q.s.f) | 1000 mL |
| B.4. - Saline citrate solution: | |
| Sodium chloride | 8.77 gm |
| Distilled water (q.s.f) | 1000 mL |
| pH adjusted to 7.4 by adding 0.056M of trisodium citrate (16.46 gm/1000 mL). | |
| B.5. - Diluent: | |
| The saline citrate solution was prepared at pH 7.4 and to it was added 1% (v/v) of deactivated bovine foetal serum and 0.1M of 2 mercaptoethanol. | |

B.6.—0.4% trypsin solution in Locke solution pH 6.9 with the purpose of partial digestion of the area of the parasite and to expose adequately the desired antigenic determinants a 4% solution of trypsin was prepared in a Locke 20 solution, 0.4 gm of trypsin (1:250) in 100 ml Locke solution or 4 gm of trypsin in 1000 mL of Locke solution (n.b. 1 ml of the promastigotes concentrate in 20 ml of the trypsin solution was added, i.e. a ratio of 1/20).

B.7.—2% formaldehyde in Locke solution at pH 6.9. 60 ml of 38% formaldehyde were mixed with 940 ml of Locke solution.

B.8.—brilliant Coomassie blue: 0.02 gm of brilliant blue Coomassie blue R-250 Merck./100 ml of saline citrate solution (n.b. Not all the Promastigotes are uniformly dyed).

B.9.—Preserving solution: 1 ml of 38% formaldehyde solution in 99 ml of saline citrate solution.

Isolation of the Parasite

1—In Vitro Culture.

To isolate the parasite, NNN medium (Novy-Nicolle-Mc-Neal) was used, see appendix(II). Every three months cultures were carried out from puncturing popliteal lymph nodes, the cultures were periodically reviewed and the results recorded.

2—Puncturing the Lymph Node.

For ease of localisation, as well as needing an only slightly traumatic methodology, it was decided to use puncturing of the popliteal lymph node as an inoculation source for the parasite. The animals were therefore immobilised and the rear part of the thigh was disinfected with alcohol and, exercising slight pressure with the fingers pressing the ganglion against the skin, it was possible to fix it on the surface Subsequently a 0.90×21 mm needle with a 5 ml syringe containing 1 ml of physiologically sterile saline solution, was introduced. Massaging the area and moving the needle, it was possible to obtain the samples.

The material thus collected was introduced into tubes containing the NNN medium, they were identified and left to incubate at 27° (Groulade and Bourdeau 1988)(WHO/LEIS/96 p28. (see appendix II).

3.—Bibliography

Groulade, P. & P. Bourdeau. 1988. Moyens practiques de mise en évidence des leihmanies. *Practique Medicale et chirugicale de l'Animal de compagnie,* 5 (supplément): 73-79.

UNDP/Word Banck/WHO. 1989. Handbook on Isolation Characterization and Cryopreservation of *Leishmania.* Geneva. pp. 145.

WHO. 1996. Manual on Visceral Leishmaniasis Control. Who/LEISH/96.40, Geneva. pp. 51-53.

Zijlstra, E. E and A. M. El-Hassan. 2001. Leishmaniasis in Sudan. *Transactions of the Royal Society of Tropical Medicine and Hygiene,* 95,S1/27-S1/58.

4.—Appendix II

Solutions and Reagents 4.1—NNN medium (Novy-Nicolle-McNeal).

The solid phase of this medium comprises 1.4 g of agar base, 0.6 g of sodium chloride (NaCl) diluted to 90 ml with distilled water. The mixture is heated until its dissolution and is sterilised at 121° C. for 15 minutes. It is left to cool to 50° C. and maintained at this temperature in a water bath with stirring. Subsequently, under sterile conditions, 10 ml of fresh defibrinated blood of rabbit, to which has been previously added 5 mg of gentamycin (Schering-Plough, España), is added. 2 ml of this is placed in tubes and the tubes allowed to cool in a horizontal position horizontal. Sterility is checked by incubation at 37° C. and once the contaminated tubes have been discard, the remainder are left under refrigeration until used.

The liquid phase of the medium is generally formed by condensation of the vapours produced by the change of temperature. In those tubes that possess very little condensation liquid, no more than five drops of PBS, physiological saline solution or even a little RPMI 1640 or 199 medium (obtained from Gibco BRL, Scotland).

| 4.2. - saline phosphate buffer solution (PBS), pH 7.2: | |
|---|---|
| Sodium chloride (NaCl) | 8 gm |
| Monopotassium phosphate (KH$_2$PO$_4$) | 0.2 gm |
| Disodium phosphate (Na$_2$HPO$_4$•12H$_2$0) | 2.88 gm |
| Potassium chloride (KCl) | 0.2 gm |
| Distilled water (q.s.f) | 1000 mL |
| 4.3. - Physiological saline solution: | |
| Sodium Chloride (NaCl) | 8.9 gm |
| Distilled water (q.s.f) | 1000 mL |

Statistical Analysis

The statistical significance ($p<0.01$ o $p<0.05$) was determined of the differences existing between the immunisation groups of dogs and regression analysis by means of ANOVA and the t test of Student.

Example 1

Construction of Recombinant Vaccinia Virus

To study the protection viability of mice susceptible to infection caused by *Leishmania*, 2 different rVV were generated: one expressing the antigen P36 of *L. infantum* (VVp36) and the other simultaneously expressing the antigen P36 of *L. infantum* and the sub-units P35 and P40 of murine IL-12 (VVp36IL12). Likewise, a control rVV was constructed that expressed the product of the env gene of HIV-1 and the sub-units P35 and P40 of murine IL-12 (VVenvIL12). In FIG. 1A, is shown the schematic representation of the genomes of these rVV.

1.1 Construction of an rVV that Expresses the Antigen P36 of *L. infantum* the gene that codifies for the protein P36 of *L. infantum* was obtained from a previously described genome library (29). It was cloned in the insertion plasmid of VV pSC11 under the control of an early/late viral promoter p7.5 in the locum of thymidine kinase (TK). This plasmid contains the, β-galactosidase gene of *E. coli* under the control of the late viral control promoter p11.

VVp36 is prepared by transfection with the previously prepared plasmid of the WR infected BSC-40 cells and the recombinant virus were collected 1 n 48-72 hours post infection and were selected after the test on plates by means of the addition of X-gal to the agar. The plates producing β-galactosidase were chosen, cloned three times and amplified using conventional procedures.

1.2 Construction of an rVV Expressing the Antigen P36 of *L. infantum* and the Murine Cytokine IL-12

The DNAc that codified for two sub-units of IL-12 (p35 and p40, were isolated, followed by an internal sequence of the attachment site to the ribosomes (IRES) from the plasmid pBSIL-12 (donated by Dr. Zavala, University de New York), by means of digestion with the restriction enzymes EcoRI and BamHI. The ends of the cassette that contained the complete sequence of IL-12 (p35-IRES-p40) were blunted by treatment with Klenow's enzyme and the cassette was cloned in the SmaI site of the insertion vector of VV pJR101. The resulting plasmid, pJR101-IL12, contains the genes of the IL-12 under the control of a synthetic early/late promoter of VV (p e/l) (39) and the marker of the β-glucuronidase of *E. coli* under the control of a synthetic early/late viral promoter (p7.5). all these sequences are flanked by regions of the hemagglutinin(HA) gene of VV.

The double recombinant VVp36IL12 was prepared by infection of BCS 40 cells with VVp36 and their transfection with the plasmid pJR101-IL12. The cell cultures were collected 48 hours after infection and the double recombinant virus were chosen after testing on plates by means of the addition of X-gluc to the agar layer (40). After three stages of selection, the virus were purified following conventional procedures by means of saccharose gradient centrifuging (41).

1.3 Construction of Control rVV

As a control, an rVV was used containing the env gene of HIV-1 (instead of the gene p36) and the codifying sequences of the subunits P35 and P40 of murine IL-12 (VVenvIL12), by means of a previously described protocol (33).

1.4 Western Analysis of Protein Expression

To confirm the protein expression of the generated recombinants of the rVV, P36 and the protein of the sub-unit P40 of IL-12, a Western transfer analysis was carried out in BCS-40 cells infected with VVp36, VVp36IL12 or VVenvIL12. In brief, BSC-40 cells (5 plate forming units (pfu)/cell) were infected with VVp36, VVp36IL12 or VVenvIL-12, and at 24 hours after infection, the cell extracts were fractionated by means of electrophoresis in a polyacrylamide gel with sodium dodecylsuphate (SDS-PAGE) under reducing conditions. They were transferred to nitrocellulose paper and made to react with polyclonal antibodies of rabbit anti-P36 (RαP36) or with monoclonal antibodies against the sub-unit P40 of IL-12 (RαP40IL12).

FIG. 1B shows that both VVp36 and VVp36IL12 but not VVenvIL12, synthesise a product that reacts with a specific antibody for P36. In the Western transfer the protein P36 derived from *E. coli*, purified with a histidine signal to compare the immune reactivity on the right hand side is shown. The difference in size with P36 expressed from the rVV is due to the extra histidine amino acids added to the extreme amine terminal.

FIG. 1C shows the immune reactivity of the same cell extracts with antibodies directed against the sub-unit of 40 kDa of IL-12. The protein twins appearing in the gel are probably related to differences of the post-translating modifications.

On the other hand, to investigate whether IL-12 expressed by VVp36IL12 and VVenvIL12 was bioactive, a biotest of IL-12 was carried out by means of a protocol described by Hogan et al. (42) with the supernatant liquids of the infected BSC-40 cells with these recombinant virus, observing that the protein IL-12 expressed by said rVV were biologically active.

the results obtained show the correct expression of P36 of *L. infantum* and of murine IL-12 in the generated rVV.

Example 2

Immunisation and Exposure to the Infection 2.1 Test I

Figure 2:
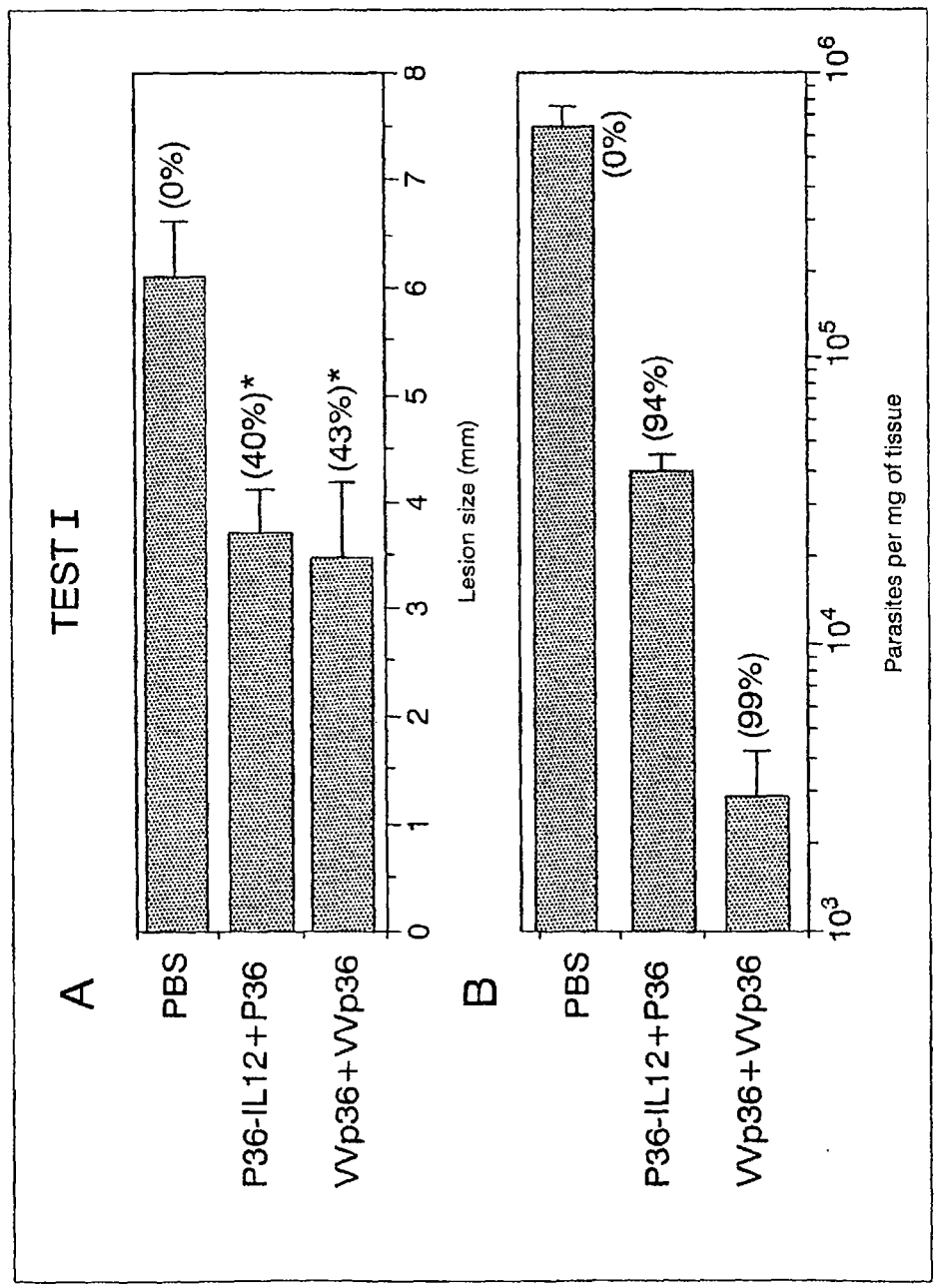

After confirming the correct expression of P36 of *L. infantum* and of murine IL-12 in the generated rVV (VVp36 and VVp36IL12), a vaccination experiment was carried out to establish whether immunisation with VVp36 induced protection in comparison with the purified protein P36 of *L. infantum* (Test I). For this, groups of 4 mice were initially treated (primed) with VVp36 ($5 \times 10^7$ pfu/mouse) intraperitoneally (i.p.) or with P36 soluble (30.mu.g). In this latter case, immunisation was carried out under optimum conditions for protection presented by other researchers (22) and, therefore, the priming included P36 together with recombinant soluble murine IL-12 (1.mu.g) (Genzyme, Cambridge, Mass.), subcutaneously (s.c.). As a control, a group of non-immunised mice was used (treated with PBS). Two weeks after the first immunisation (14 days post immunisation (dpi)), the animals were administered a booster dose with either soluble P36 (30.mu.g) or with VVp36 ($5 \times 10^7$ pfu/mouse). Three weeks later, the animals were exposed to $10^5$ promastigotes of a frozen mother solution of *L. major* administered in the cushion of the right hind paw and the development of the lesions was measured at the site of the inoculation weekly until 7 weeks after exposure (12 weeks after the initial dose), with digital callipers (Mauser Digital, Switzerland), being expressed as the increased thickness of the infected hind leg in comparison with the non infected hind leg. The parasite load was also measured in the lymph nodes of the animals 7 weeks after exposure to the parasite by means of the protocol described in the Materials and methods section. The results obtained among the different animal groups were compared, which were presented as the reduction in the size of the lesion and the parasite load in comparison with a non-immunised group (control with PBS). FIG. 2A shows the average size of the lesion of each immunisation group, whereas FIG. 2B shows the parasite load in the lymph nodes. The results obtained show that the protein P36 of *L. infantum* administered as a soluble protein, as well as that expressed by VVp36, were able to induce a degree of protection against *L. major* in comparison with those non-immunised animals. In those animals immunised with VVp36, there seems to be a greater parasite reduction effect than the animals that received the soluble protein.

2.2 Test II

As murine IL-12 increases the cellular immune response to an antigen and leads the immune system to a Th1 response (4446), the adjuvant power of IL-12 has been studied when it is co-expressed together with P36 (Test II). In order for the results to be significant, the number of animals was increased to 10 per group (four animals were killed before exposure to carry out immunological studies). 6 groups of animals were used:

The control group received PBS.
The second group received the soluble antigen of *L. major* (LSA).
The third group received VVp36IL12.
The fourth group received VVp36IL12.
The fifth group received VVp36.
The sixth group received VVenvIL12.

The mice were administered an initial dose of rVV ($5 \times 10^7$ pfu/mouse) via i.p. or of P36 of recombinant *L. infantum* (30 μg/mouse) via s.c. Two weeks after the first immunisation, i.e. at 14 days dpi, each group of animals were administered a booster dose with homologous immunogens, except the third group, which received soluble P36. Three weeks after the booster (34 dpi) sera, spleens and lymph nodes were obtained from each immunisation group. The following day (35 dpi), all the mice were exposed to $5 \times 10^4$ promastigotes of metacyclic virulent virus of *L. major* in stationary phase which was administered in the cushion of the right hind paw. The development of the lesions was measured weekly at the inoculation site with digital callipers (Mauser Digital, Switzerland), being expressed as the increase in thickness of the infected hind leg in comparison with the non-infected hind leg, as well as the parasite load until 7 weeks after exposure to the promastigotes. At the end of the experiments (7 weeks after exposure) the mice were killed and sera, lymph nodes and spleens were taken to carry out immunological tests.

Figure 3:
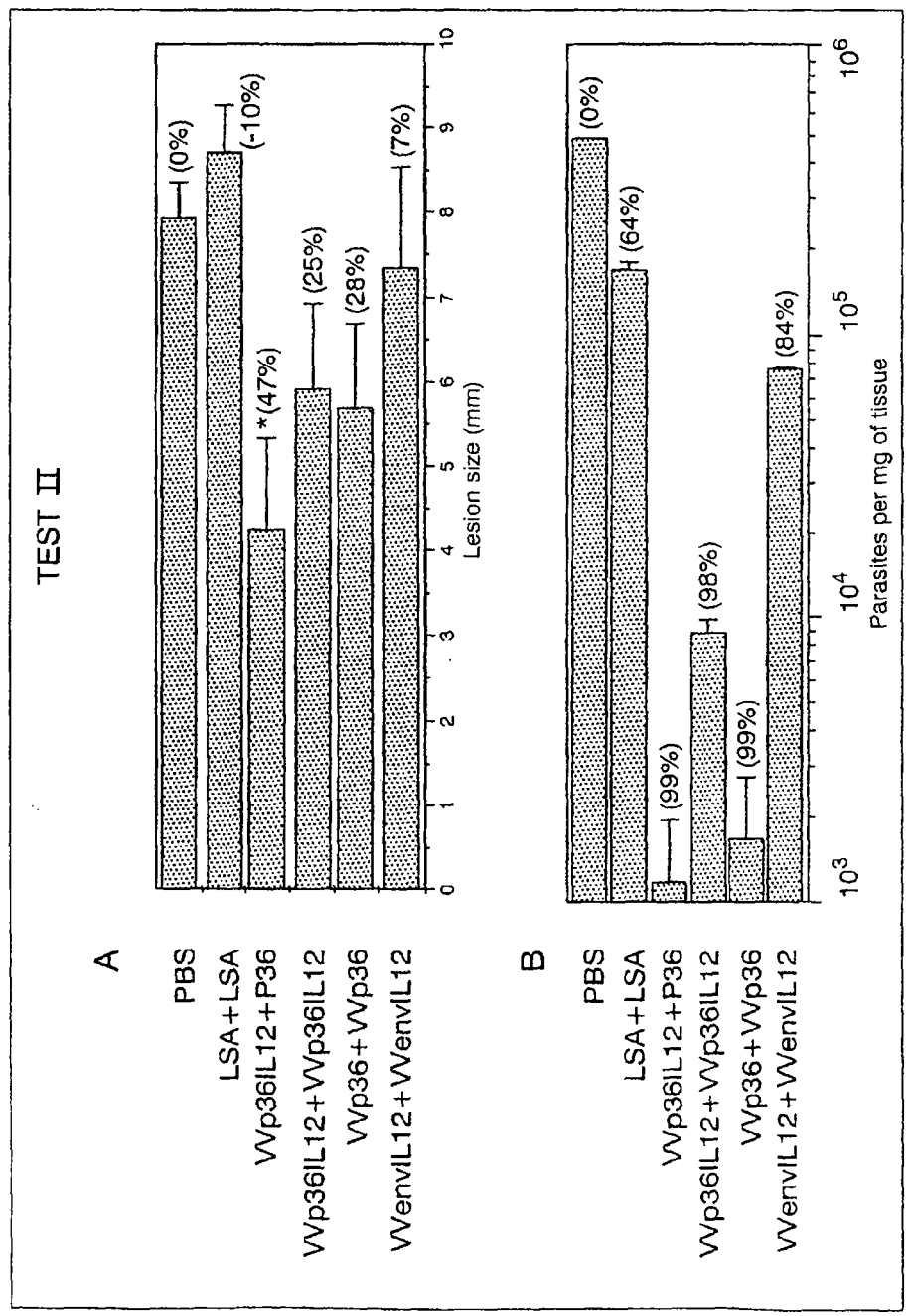

FIG. 3A shows the mean size of the lesion and FIG. 3B shows the mean of the parasite load. in the draining lymph nodes nearest the lesion. Although the control group (PBS) developed severe infection, the groups (VVp36+VVp36) and (VVp36IL12+VVp36IL12) were able to control the infection to some amount, as a reduction in the size of the lesion and the parasite load was discovered. The best immunisation protocol comprised the administration of VVp36IL12 as the initial immunogen followed by soluble P36. In this group, the mean size of the lesion 7 weeks after exposure was significantly less than the remainder of the groups (mean reduction of 47% in comparison with the control group) and, at the same time, the parasite load was notably reduced (99%).

The double immunisation with VVp36IL12 did not improve the results obtained over those with a single dose. The size of the lesions was only reduced by 25% compared with the control group. The parasite load found in this group of animals was maintained relatively low ($8.9 \times 10^3$ parasites/mg), although higher than the group of animals that had been protected in the best way (VVp36IL12+P36: $1.1 \times 10^3$ parasites/mg). It must be emphasised that similar results were obtained with the non-immunised mice (PBS) and the VV control mice (VVenvIL12). This observation indicates that infection with VV does not help exacerbate the course of the parasitic infection.

The results obtained in this test show that the rVV that co-expresses P36 and IL-12 (VVp36IL12) induces greater protection against *L. major* than VVp36.

2.3 Test III

As in the previous immunisation experiment (Test II) significant protection was obtained against *L. major* with a protocol based on the sequential administration of the immunogens VVp36IL12 followed by soluble P36. It was then determined whether the inverse immunisation protocol could also induce protection against *Leishmania* (Test II), since, as is well known, rVV administered in a booster dose expands the primary $CD8^+$ T cells (66). In order for the results to be significant, the number of immunised mice per group was increased to 12. Four groups of animals received initial and booster doses with different combinations of immunogens and were exposed by means of a similar procedure to that described for Test II.

Figure 4:
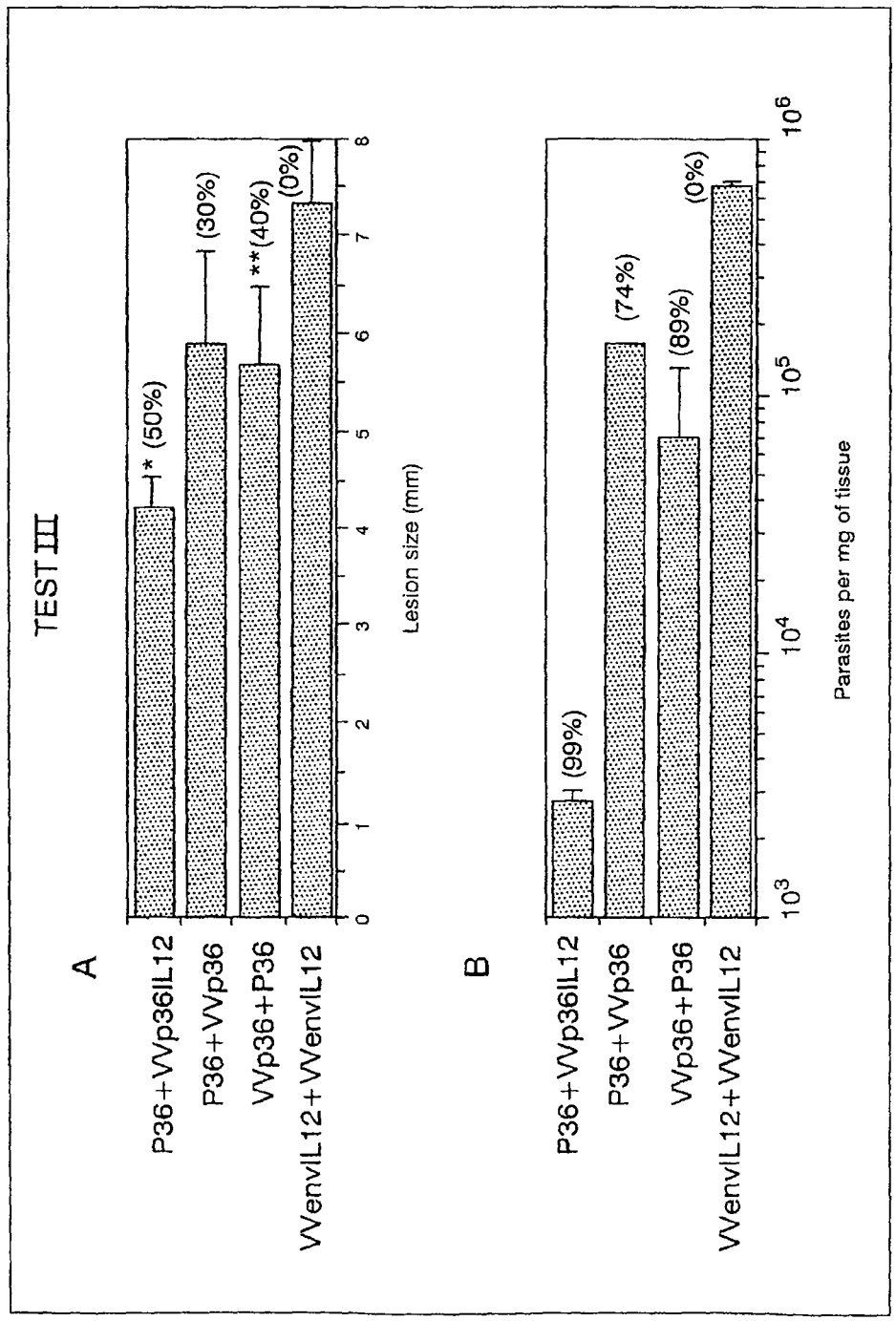

In FIG. 4 are shown the results that indicate the effect of the different immunisation protocols on the size of the lesions and the parasite load. The group P36+VVp36IL12 showed a reduction of approximately 50% in the size of the lesion (3.77±0.31 mm) compared to the control group (VVenvIL12+VVenvIL12: 7.61±0.62 mm). The second best group was that with VVp36 plus soluble P36 (reduction of 40%; 4.53±0.80 mm). N this experiment, the opposite protocol (P36+VVp36) only provided a reduction of 30% (5.38±0.95 mm). When the parasite load was measured, it was found to be notably less (99%) in animals immunised with P36+VVp36IL12.

2.4 Test IV

Figure 5:
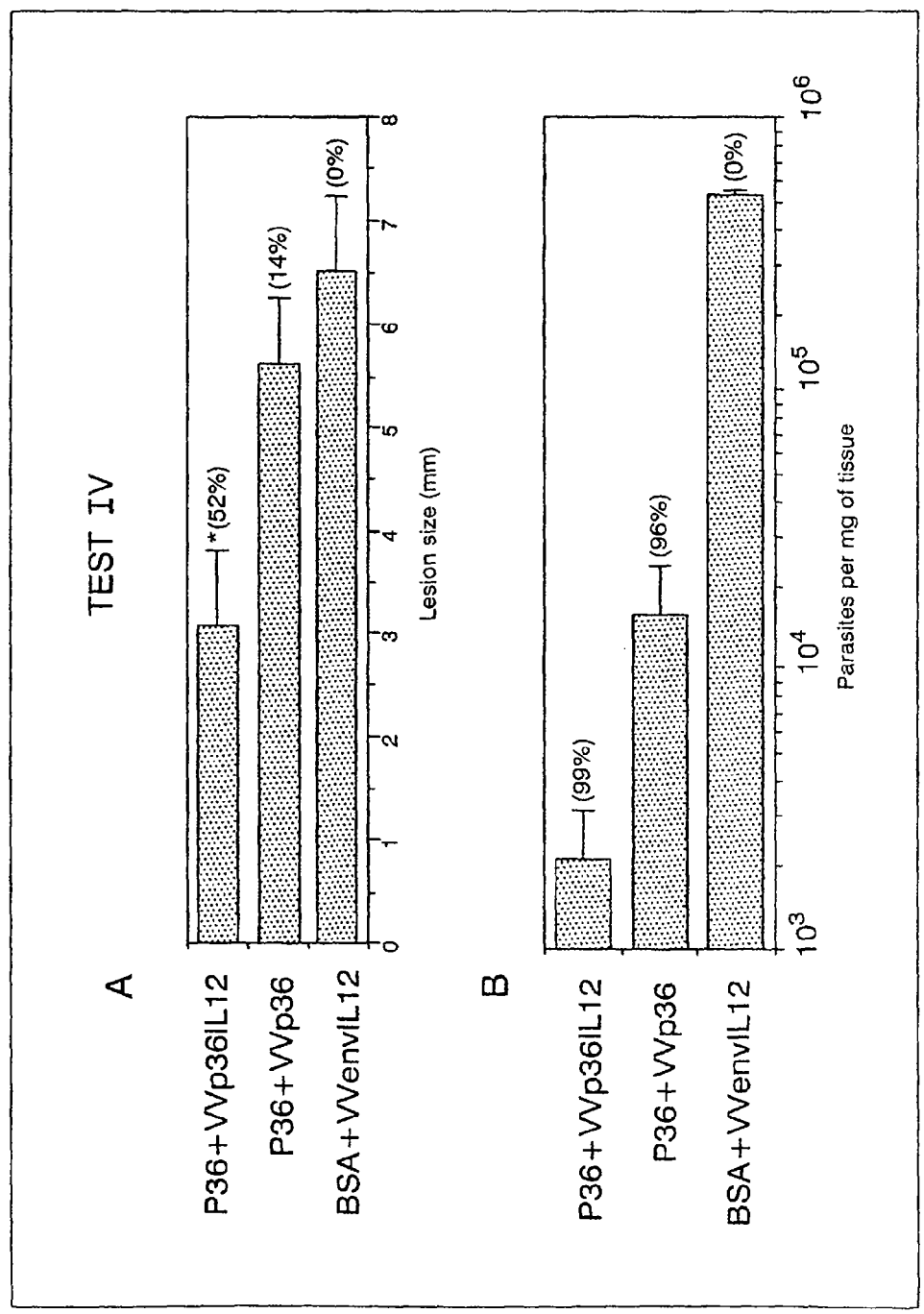

To demonstrate further that the protection afforded by means of the protocol P36+VVp36IL12 is very significant, another experiment was performed with 13 animals per group and the protective efficacy was compared with animals immunised with P36+VVp36 (Test IV) following a procedure similar to that described in Test II. In FIG. 5 the results are shown for the size of the lesions and the parasite load. In those animals immunised with P36+VVp36IL12 a reduction in the size of the lesions and in the parasite load was clearly seen, greater than that in the animals immunised with P36+VVp36.

The results shown in FIGS. 4 and 5 allow it to be established that of the different immunisation protocols tested, that which began by administering the soluble protein P36 followed by a booster with VVp36IL12 induced the greatest protection against infection caused by L. major.

Example 3

Characteristics of the Immune Response Produced by Different rVV Before and after Exposure to Promastigotes of L. major 3.1 Humoral and Cell Immune Responses Before and after Exposure to L. major The immune response provoked in mice susceptible to infection by Leishmania is of the type Th2 and this response has been co-related with the progress of the disease (47-49), whereas the production of cytokines such as IFN-γ and IL-12 has been co-related with the resolution if the disease (50, 51). So as to induce protection against Leishmania infection(10, 11) could require the activation of an immune response of the type Th1, the type of immune response generated before immunisation with the rVV generated has been determined. For that, the researchers characterised the relation between a characteristic response of type Th1 with majority production of IgG of isotype 2a and IFN-γ) (52) and a response of type Th2 (with majority production of IgG of isotype 1 and IL-10) in the groups of mice immunised with the regime of an initial dose and a booster dose as has been described in Example 2. Three weeks after the booster, serum was extracted from each group of animals and the levels of specific immunoglobulins G anti-P36 (of isotypes 1 and 2a) were evaluated in the groups collected. The results for the animals used in Tests HIV (Example 2) are shown in table 1.

TABLE 1

Specific production of IgG1, IgG2a, IFN-γ and IL-10 after exposure to L. major

| | IgG2a/IgG1[a] | IFN-γ[b] | IL-10[b] | IFN-γ/IL-10 |
|---|---|---|---|---|
| Test II | | | | |
| VVenvIL12 + VVenvIL12 | 0 | 175 ± 30 | 70 ± 8 | 2.5 |
| VVp36 + VVp36 | 0.86 | 2,345 ± 100 | 166 ± 23 | 14.1 |
| VVp36IL12 + P36 | 1.04 | 2,432 ± 160 | 139 ± 97 | 17.4* |
| VVp36IL12 + VVp36IL12 | 1.05 | 2,787 ± 160 | 58 ± 6 | 48.05* |
| LSA + LSA | 0/0.35 | 257 ± 30 | 676 ± 33 | 0.38 |
| PBS + PBS | 0 | 62 ± 2 | 61 ± 5 | 1 |
| Test III | | | | |
| VvenvIL12 + VvenvIL12 | 0 | 177 ± 24 | 91 ± 9 | 1.94 |
| VVp36 + P36 | 1.52 | 1,985 ± 125 | 251 ± 58 | 7.90 |
| P36 + VVp 36 | 0.47 | 3,070 ± 309 | 301 ± 78 | 10.19 |
| P36 + VVp36IL12 | 1.81 | 2,659 ± 38 | 120 ± 56 | 22.15* |
| Test IV | | | | |
| BSA + VvenvIL12 | 0 | 67 ± 5 | <15 | 0 |
| P36 + VVp36 | 0.42 | 1,730 ± 73 | 100 ± 10 | 17.30 |
| P36 + VVp36IL12 | 2.34 | 2,964 ± 124 | 90 ± 15 | 32.93* |

[a]IgG2a/IgG1 represents the absorbance relations 492 nm of specific antibodies of each immunisation group diluted 1:100, as is determined by an indirect ELISA. Each value represents the mean of two independent determinations ± SD for the samples taken (Test II, n = 4, Test III, n = 4; Test IV, n = 6). The sera were taken 7 weeks after exposure to the parasite.
[b]Spleen cells were taken of each immunised mouse group 7 weeks after exposure and cultured with soluble protein P36 at a concentration of 2 µg/ml for 48 hours. The production of cytokines was determined from the supernatant liquids of the culture, as is described in the Materials and Methods section. Each value represents the mean ± SD of two different determinations.

As was expected, all the mice groups immunised with rVV developed a specific immune response against VV proteins in an ELISA test (data not shown), which indicates that the immunisation procedure was correct. The immunisation protocols based on soluble protein P36 together with VVp36IL12 (Tests III and IV) obtained the best overall relation (IgG2a/IgG1 of 1.81 and 2.34 respectively). On the other hand, the mice group immunised with LSA (Test II) provided the greatest quantity of specific IgG1. This is coherent with the results in the size of the lesions and in the parasite load for this group of mice, which indicates that LSA preferentially induces a type Th2 response before exposure (53).

With respect to the cellular immune response, all the animal groups immunised with VVp36 or VVp36IL12 produced large quantities of IFN-γ in comparison with the levels of IL-10. Considering the relation of IFN-γ/IL-10 (Table 1), only those animals immunised with VVp36IL12 developed significantly high levels (p<0.01) in comparison with the control groups, which indicates a specific activation of a Th1 type response in these animals. Clearly, the protocols that included VVp36IL12 as an immunising vector provoked a Th1 response defined by high quantities of specific IgG2a and IFN-γ.

In general, after in vitro specific stimulation of the spleen cells before exposure to the parasite, those mice initially immunised with P36 followed by VVp36IL12 produced the largest quantities of IFN-γ and the smallest quantities of IL-10. Significantly, a double immunisation with VVp36IL12 (Test II) produced a high production of IFN-γ but also a high production of IL-10 after exposure, which could explain why this protocol is unable to improve the results of protection obtained with a single immunisation with VVp36IL12. Coherently, the greater relation IFN-γ/IL-10 before exposure to the parasite was obtained after immunisation with immunisation protocols containing VVp36IL12.

3.2 Humoral and Cellular Immune Responses after Exposure to L. major

Since the consequences of the illness can be determined by the degree of activation of the immune system, the characterisation of the changes in relative to immunoglobulins and cytokines after exposure of the previously rVV immunised animals is of interest. Thus, 7 weeks after exposure to the promastigotes, the mice were killed, spleens and sera were taken from each group and the production of specific IFN-γ e IL-10 were evaluated (Table 2).

TABLE 2

Specific production of IgG1, IgG2a, IFN-γ and IL-10 after exposure to L. major

| | IgG2a/IgG1[a] | IFN-γ[b] | IL-10[b] | IFN-γ/IL-10 |
|---|---|---|---|---|
| Test I | | | | |
| VVp36 + VVp36 | 0.99 | 4,035 ± 116 | 226 ± 23 | 17.85 |
| P36-IL12 + P36 | 0.50 | 1,790 ± 134 | 196 ± 30 | 9.13 |
| PBS + PBS | 0.31 | 193 ± 23 | 541 ± 74 | 0.35 |
| Test II | | | | |
| VVenvIL12 + VVenvIL12 | 0.62 | 1,906 ± 175 | 470 ± 32 | 4.05 |
| VVp36 + VVp36 | 1.16 | 4,451 ± 156 | 532 ± 53 | 8.36 |
| VVp36IL12 + VVp36IL12 | 1.66** | 3,387 ± 147 | 725 ± 14 | 4.67 |
| VVp36IL12 + P36 | 1.39** | 3,566 ± 500 | 107 ± 17 | 33.32* |
| LSA + LSA | 0.17/1.08 | 20 ± 12 | 357 ± 26 | 0.56 |
| PBS + PBS | 0.12/0.23 | 17 ± 7 | 169 ± 46 | 0.10 |

TABLE 2-continued

Specific production of IgG1, IgG2a, IFN-γ and IL-10 after exposure to *L. major*

| | IgG2a/IgG1[a] | IFN-γ[b] | IL-10[b] | IFN-γ/IL-10 |
|---|---|---|---|---|
| Test III | | | | |
| VvenvIL12 + VvenvIL12 | 0.62 | 1,254 ± 19 | 705 ± 85 | 1.77 |
| VVp36 + P36 | 1.66 | 3,178 ± 203 | 354 ± 25 | 8.97 |
| P36 + VVp36 | 0.57 | 1,979 ± 249 | 669 ± 36 | 2.95 |
| P36 + VVp36IL12 | 2.62** | 3,541 ± 94 | 241 ± 35 | 14.69* |
| Test IV | | | | |
| BSA + VvenvIL12 | 0.78 | 520 ± 5 | 400 ± 93 | 1.30 |
| P36 + VVp36 | 0.91 | 2,046 ± 68 | 244 ± 52 | 8.38 |
| P36 + VVp36IL12 | 1.45** | 3,075 ± 125 | 165 ± 12 | 18.63* |

[a]IgG2a/IgG1 represents the relation of absorbances at 492 nm of specific antibodies for each immunisation group diluted 1:100, as is determined by an indirect ELISA. Each value represents the mean of two independent determinations ± SD for the samples taken (Test I, n = 4, Test II, n = 6; Test III, n = 8; Test IV, n = 10). The sera were taken 7 weeks after exposure to the parasite.
[b]Spleen samples were taken from each immunised group of mice 7 weeks after exposure and were cultured with soluble P36 protein at a concentration of 2 μg/ml for 48 hours. Cytokine production was determined from the supernatant liquid of the culture, as is described in the Materials and Methods section. Each value represents the mean ± SD of two different determinations.

Analysis of the levels of specific IgG (isotypes 1 and 2a) revealed that significantly high (p<0.05) relations in the group of mice immunised with VVp36IL12. Likewise, the largest relation IgG2a/IgG1 was obtained after immunisation with VVp36IL12 (Test II: 1.66, 1.39: Test III: 2.62 and Test IV: 1.45). Considered jointly, these results reveal an inverse correlation between the specific IgG2a/IgG1 relation of P36 and the size of the lesions (r=0.63, p<0.01), as well as between parasite loads and specific IgG2a (r=0.56, p<0.01), which confirms that the animal models behaved as previously described (7, 10, 11).

Coherently with the results obtained from the samples tested before exposure to the parasite, double immunisation with VVp36IL12 revealed high levels of type Th1 and Th2 cytokines (six times more IL-10 than a single dose with VVp36IL12; Test II). This data could explain in part the differences of protection observed (25% against 47% of the reduction of the lesion). Considering all the data of the 3 tests (II, III and IV), the mice immunises with VVp36IL12 provided significantly (p<0.01) the largest relation IFN-γ/IL-10 in comparison with the control groups. The protocols based on VVp36 also provided high relations but did not reach statistically significant differences in comparison with the control groups. The fact that repeatedly high production levels of the cytokines studied in mice of the control groups with VV (VVenvIL12) at seven weeks after exposure to the parasite is interesting. This could be due to a nonspecific production of cytokines after exposure b the parasite, since high levels were also found in the negative controls (spleen cells of the same group of mice cultured in the absence of a stimulus, data not shown).

Example 4

Construction of Recombinant Vaccinia Virus

To study the viability of the protection of susceptible dogs from infection caused by *Leishmania*, a rVV was generated that expressed the P36 antigen of *L. infantum* (VVp36) in the same way as is described in Example 1 of this invention.

4.1. Construction of the Vector pRSET-B

On the other hand, the plasmid pRSET-B (pCI-neo/p36/LACK) is constructed from the plasmid pCI-neo of Promega®, by means of the insertion of the codifying sequence of the protein p36 of *L. infantum* in said plasmid with the restriction enzyme EcoRI at the 5' end and Sma I at 3'.

4.2 Western Analysis of Protein Expression

To confirm the recombinant protein expression of the generated rVV, P36 in BCS-40 cells infected with VVp36, a Western transfer analysis was performed. In brief, BSC-40 cells (5 plate forming units (pfu)/cell) were infected with VVp36 and at 24 hours after infection, the cellular extracts were fractionated by means of electrophoresis in polyacrylamide gel with sodium dodecylsulphate (SDS-PAGE) under reducing conditions. They were transferred to nitrocellulose paper and made to react with polyclonal antibodies of rabbit anti-P36 (RαP36). The results obtained show the correct expression of P36 of *L. Infantum*, since VVp36 synthesises a product that reacts with a specific antibody for (data not shown).

Example 5

Test of p36/LACK as a Vaccine Against Leishmaniasis Induced by *L. infantum* in Dogs After confirming the correct expression of P36 of *L. infantum* in the generated rVV (VVp36) and by the plasmid pRSET-B (pCI-neo/p36/LACK), a vaccination experiment was carried out to establish whether immunisation with pRSET-B and VVp36 induced protection. The dogs from the protection groups were immunised with two doses, either with the plasmid pRSET-B (400 μg en total) in two separate doses separated by an interval of two weeks (group P+P) or with a dose of plasmid pRSET-B (200 μg) and another dose of VVp36 ($10^8$ pfu) after two weeks (group P+V) (Table I). The dogs were divided into four groups of five dogs each. The groups were respectively designated as:

Negative control: without prior protection treatment or inoculation with the parasite.
Positive control: without prior protection treatment and inoculated with the parasite.
Group P+P: Immunised with the plasmid pCI-neo/p36/LACK (pCI-neo of Promega), which contains the complete codifying sequence for the antigen p36/LACK of *L. infantum*. Two doses of 100 μg were administered subcutaneously in a 15 day period in saline solution.
Group P+V: Immunised with an initial dose of 100 μg subcutaneously of the same vector and a second dose 15 days afterwards with the vaccinia virus (strain WR, attenuated), which contained a complete copy of the gene that codifies for p36/LACK (VVp36). $10^7$ pfu were administered subcutaneously.

Immediately afterwards, they were experimentally infected with $10^8$ promastigotes of *L. infantum* (MHOM/FR/78/LEM-75) intravenously after two weeks from the protection treatment with the recombinant vehicles(day zero) at the same time as the control groups were infected (day 0 of the experiment).

The dogs were previously analysed for their haematological constants, they were followed up daily for their physical state, food intake and general condition. In order to learn the type of immune response being produced in the animals, every 15 day peripheral heparinised blood samples were taken from day zero until day one hundred and twenty-nine. From these samples, mononuclear cells (PMBC) were obtained by means of centrifuging in a Ficoll gradient (Histopaque®, Sigma). A sample of plasma was also obtained. The total RNA was extracted using Trizol® in accordance with the manufacturer's instructions, In each experiment and in parallel, as an internal control, the levels of glyceraldehyde dehydrogenase (GAPDH) were detected. The RT-PCR technique was used for detection of the mRNA levels of the interleukins IL4 and IFNγ, related to the proliferation of the subpopulations of Th2 and Th1 respectively.

The samples obtained were allowed to run in agarose gels (2.0%) and the band intensity was analysed by means of the Scion Image for PCprogram of the National Institutes of Health, USA. Determinations were always performed in duplicate and each point of determination in the graphs is the mean of five determinations (one for each animal of the group). The presence of specific antibodies anti p36/LACK and its class: IgG2 (corresponding to the proliferation of the Th1 subpopulation of lymphocytes (CD4+) and IgG1 (corresponding to the Th2 subpopulation were determined in the corresponding plasma samples. The specific antibodies were determined by means of the ELISA technique using plates of 96 wells (Maxisorp®, Nunc). Reading was performed with the Fluostar program of Galaxy-BMG-Labtechnologies. In each case the values (in arbitrary units) represent the mean of the values with reference to their internal control.

Figure 6:
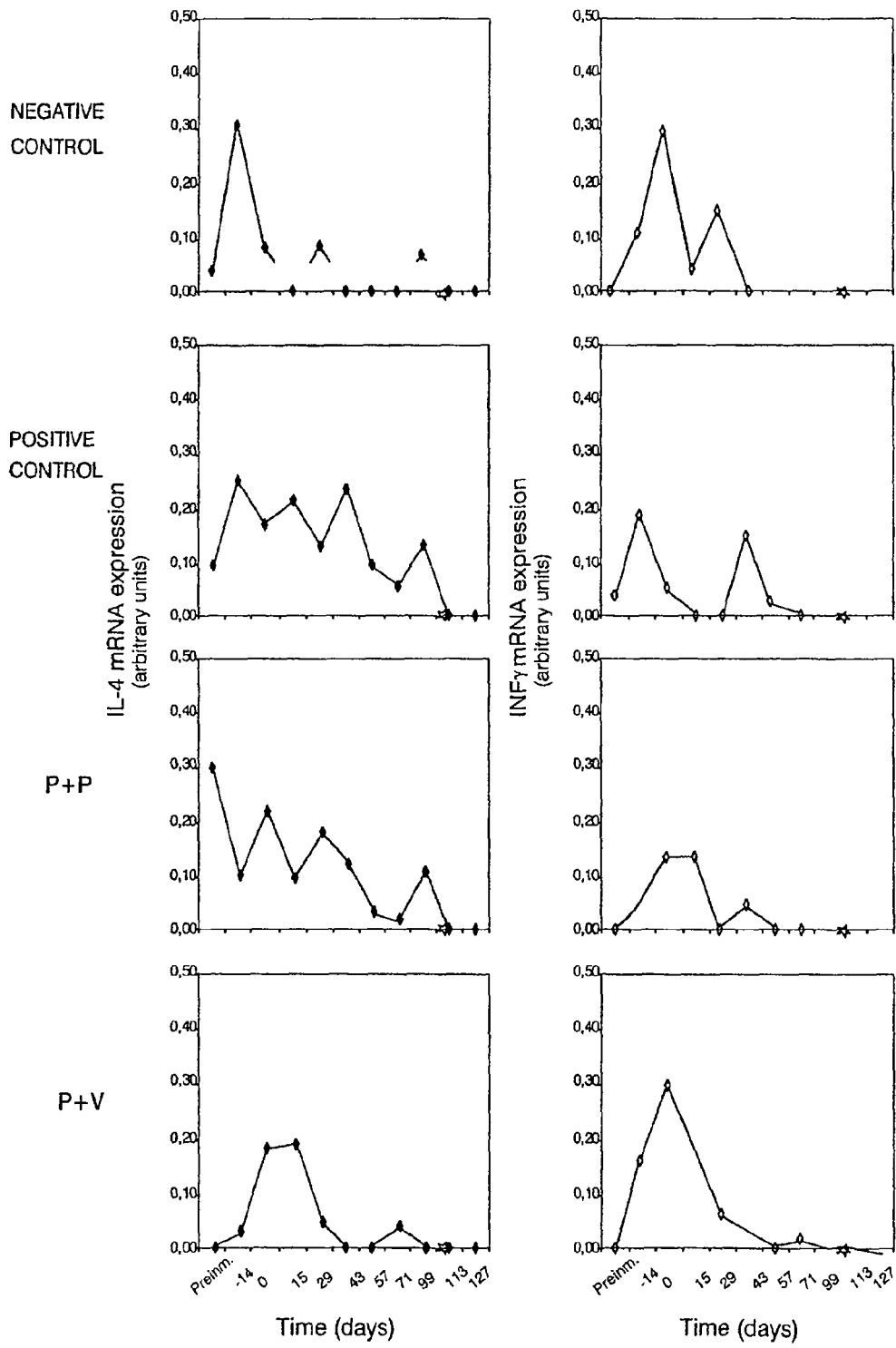
Figure 7:
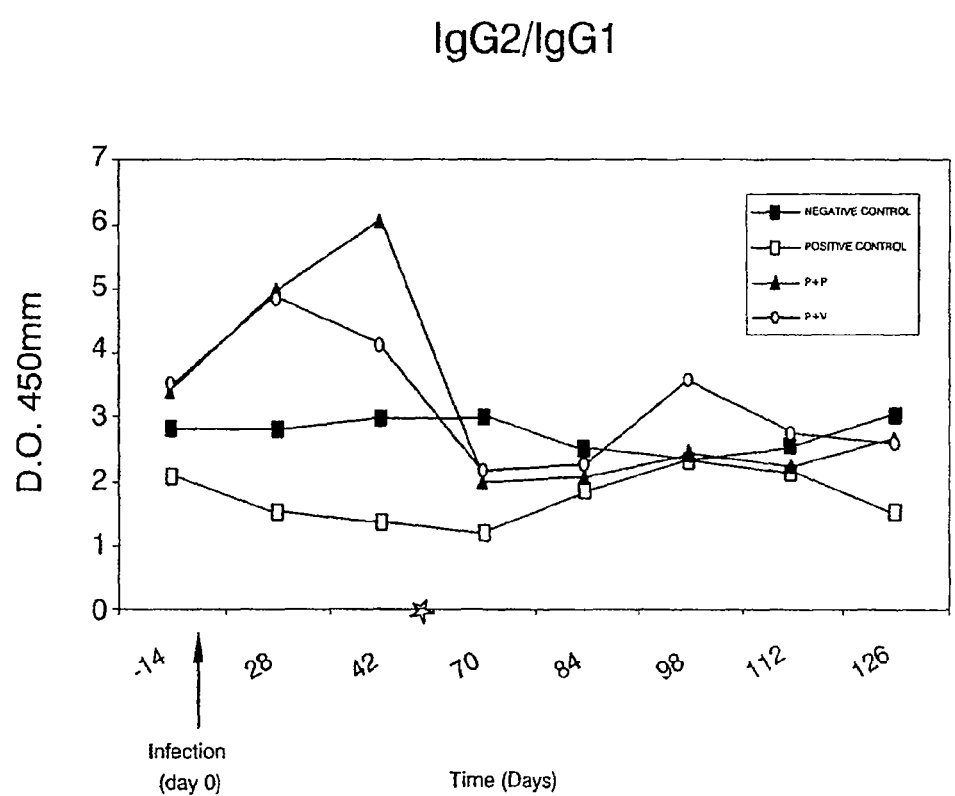

The results obtained are shown in FIGS. 6 and 7 and in Table 3. Table 3 shows the clinical data of the disease in the dogs, as well as the data foe serological positivisation and the isolation of the parasite in those clinically diseased dogs. Four clinical signs are considered and they normally define the clinical disease: Presence of lymphadenopathies (L), Muscular atrophy (AM), Paleness of the mucous membranes (PM) and skin lesions (LP). As can be observed, the negative control group (not vaccinated not infected) is negative in 100% of the cases that show no clinical sign nor any type of serologically positive test. The positive control group (infected, not vaccinated) shows the presence of clinical signs of the disease in 100% of cases. Positivisation of the serological tests also is 100% and the parasite has been able to be isolated in 60% of the cases. Serological positivisation was sequential in all cases, being the DAT method of agglutination of *Leishmania* antigens (72) the mostreliable with no false positives and a sequential progression of the titles of the anti-sera with the progression of the infection. The group vaccinated with two doses of the gene p36 in a pRSET-B recombinant plasmid before experimental infection shows the presence of clinical signs of the disease in all cases (Some of them with only one of the four considered as defining the disease). The serological tests were also positive in nearly all cases and the parasite was recovered in nearly all the dogs showing clinical symptoms. The group vaccinated with two doses of the gene p36, one the plasmid PRSET-B (P) and another in the VVp36 (V) before infection, induced protection against infection in at least 60% of cases (one dog had only one clinical symptom and no positive serology but, although it is a lymphadenopathy that could be due to another non-specific reason, it has been shown as positive). Only one of the dogs showed clinical signs of the disease, positive serology with the parasite being able to be isolated from it.

TABLE 3

Results observed in the 18$^{th}$ month of the test corresponding to the 15$^{th}$ month post infection

| GROUP | Dog N° | Serological tests | | Parasite isolation (NNN medium) | Clinical signs** | | | |
| --- | --- | --- | --- | --- | --- | --- | --- | --- |
| | | DAT* | Commercial kit*** | | L | AM | PM | LP |
| NEGATIVE CONTROL | 5 | − | − | − | − | − | − | − |
| | 7 | − | − | − | − | − | − | − |
| | 7408 | − | − | − | − | − | − | − |
| | 7446 | − | − | − | − | − | − | − |
| | 7372 | − | − | − | − | − | − | − |
| POSITIVE CONTROL | 1 | + | − | − | + | + | + | + |
| | 2 | + | + | + | + | + | + | + |
| | 3 | + | + | − | + | + | + | + |
| | 7318 | + | + | + | + | + | + | + |
| | 7334 | + | + | + | + | + | + | + |
| P + P | 4 | + | + | + | + | + | + | + |
| | 6 | + | + | + | + | + | + | + |
| | 7338 | + | + | − | − | − | − | + |
| | 7414 | + | + | + | + | + | − | + |
| | 7450 | + | + | + | + | − | − | − |
| P + V | 8 | − | − | − | − | − | − | − |
| | 9 | − | − | − | − | − | − | − |
| | 10 | − | − | − | − | − | − | − |
| | 7350 | − | − | − | + | − | − | − |
| | 7440 | + | + | + | + | + | + | − |

*values from 1/800 were considered positive.
**Clinical signs: L: lymphadenopathy; AM: muscularatrophy; PM: pale mucous membranes; LP: skin lesions.
***Detects antibodies against the surface antigens of Leishmania.

5.1.—Production of IL 4 and IFN-γ by the Peripheral Blood Cells

As can be observed, the cytokine expression considered shows a variation during the course of the experiment, fundamentally due to the variability of the individual response. In any case, several tendencies in their expression may be drawn. Thus, interleukin 4 (IL4) shows high mean values in the positive control group (animals without protection to canine leishmaniasis induce experimentally). These values remain high throughout the experiment (until day 113) and above those determined for gamma interferon (IFN gamma) that shows only two indeterminate increases. This suggest a predominance of the Th2 subpopulation over that of the Th1 in dogs that show the disease established in all cases. The group vaccinated with a plasmid containing the gene p36/LACK and the virus VVp36 containing the same gene shows a more rapid increase in the values of gamma interferon (IFN gamma) than those of interleukin 4 (IL 4) in the first weeks following immunisation, coinciding with the inoculation of the parasite. This would indicate a predominance of the Th1 subpopulation over the Th2 in this group of dogs that has shown a high degree of protection against the disease (see Table 3).

5.2.—Determination of Specific Antibodies Anti p36/LACK in the Sera of the Dogs

FIG. 7 shows the relation between the specific antibodies anti p36/LACK in the groups of dogs throughout the experiment. The existence of a humoral response is clear with specific antibodies anti p36 in the groups of dogs that were vaccinated that were not present in the control groups (without vaccination)). The response, with the presence of specific antibodies anti p36/LACK, appears during the first 75 days of the experiment and the predominance of the production of IgG2 over IgG1 can also be seen indicating a predominance of the cellular Th1 response over the Th2. These agree with the previous data on the cytokines. It is interesting to note that this does not occur in the corresponding control groups, either negative or positive, showing an equilibrium between the levels detected of the antibodies IgG1 and IgG2. These results indicate that in the vaccinated groups of dogs a specific antibody response has been produced against the protein codified by the gene introduced in recombinant vehicles. The type of response indicates that the type of CD4+ cells that have proliferated is the Th1.

5.3.—Protection Test Against Infection by *Leishmania infantum*.

As well as the studies on the production of interleukins and specific antibodies to learn the factors that reflect the type of immune response, the study of evolution of the infection and disease has been carried out in the groups of dogs which were the object of the study. The presence of antibodies against the antigens of *Leishmania* has been measured, DAT by means of direct agglutination, habitually used as a diagnostic method. Another specific test kit (kit of Operon S.A.), which measures the existence of anti-surface antibodies of *Leishmania* was used. The clinical evolution of the dogs was measured throughout the period using four universally accepted clinical criteria: the existence or not of lymphadenopathies, muscular atrophy, paleness of the mucous membranes and the existence of skin lesions. Likewise, it was attempted to isolate the parasite in NNN medium from the ganglia of dogs with positive serology and clinical symptoms.

The experiment was considered finished in the eighteenth month post infection at the time when all the dogs in the positive control group showed clinical signs of the disease and positive serology.

At that moment the positive control group showed 100% of the dogs with positive serology and clinical signs of the disease. The negative control group had 100% of the dogs without any sign of the disease and with negative serology. Of the two vaccinated groups, the group of the two doses of the vaccine in plasmidic vehicle had positive serology and variable clinical signs of the disease.

The group vaccinated with two doses of the codifying gene for p36/LACK, one with the plasmid pCI-neo and the second with the gene introduced in recombinant vaccinia-WR virus, gave negative results in the diagnostic methods in 80% of cases and an absence of clinical signs in at least 60% of cases (there is one case of the presence of lymphadenopathies).

Thus, it seems that the dogs of group P+V, i.e. those vaccinated with a doss of the gene in the plasmid pCI-neo/p36/LACK and the second with the gene a vaccinia virus-WR/p36/LACK show protection against experimental infection in at least 60% of cases with respect to the positive controls, which showed infection and clear clinical signs in 100% of the cases.

Discussion

During a natural infection, the fly *Phlebotomus*, by means of a bite, transfers through the skin promastigotes to the vertebrate host. Within the macrophages, the promastigotes are transformed rapidly in dense round organisms (amastigotes), which remain in the host throughout the life of the parasite. The control of the infection requires the depending activation of the T cells of the macrophages to achieve an antiparasitic state capable of stopping the infection. The studies carried out on mice, in which certain genes (54, 55) have been removed and other immunological procedures have defined the requirements for the class II major histocompatibility complex (MHC) and $CD4^+$ T cells (56), as well as the effector cytokine IFN-$\gamma$ (44), the Th1 mediator cytokine IL-12 (16), and macrophageal microbicide enzyme, type 2 nitrous oxide synthase (NOS2), in the control of the infection (57, 58). In this scenario, the presentation of epitopes derived from parasites in molecules of MHC class II to the $CD4^+$ T cells induces differentiation to a type Th1 cell with the production of IFN-$\gamma$ and its increase by IL-12. at the same time, the production of IFN-$\gamma$ causes the induction of the NOS2 of the macrophages and the repression of the parasitic infection (59, 60).

Balb/c mice provide a an ideal system for studying infection *Leishmania*, since they maintain the infection, this leading eventually to death. The lesions and the series of infections produced in mice susceptible to *L. major* are quite similar to those produced in human beings (5). Therefore, *L. major* is a very good model for testing vaccination. It has been demonstrated that the production of a solid type of immune response type Th1, protection can be achieved in the mouse model and that the infection is correlated with the response of the abnormal $D4^+$. This immune state of the mouse could imitate what occurs in the human host and probably in dogs. The conventional ways to create vaccines against parasitic diseases have been mostly unsatisfactory. It is now evident that immunological means in which an immune response is initiated are probably more important than the antigen used (61). It has been shown that immunisation with some defined antigens (soluble gp63 of *L. major* or soluble LSA of *L. major*) could have some protective effect only when these proteins are administered jointly with IL-12 (62).

In an attempt to lead the immune response to the type Th1 and achieve protection against leishmaniasis, several immunisation strategies in Balb/c mice have been compared, using as an immunogen the antigen LACK of the parasite (protein P36) and as a liberation vector to the VV. Recombinant virus have been generated that only express P36 (VVp36) or that co-express P36 and IL-12 (VVp36IL12) and they have been tested in mice in relation to their capacity to induce a protective immune response after exposure to the promastigotes. The inventors have discovered that, although mice immunised with VVp36 develop a significant protection against the parasite, immunisation with VVp36IL12 induces greater levels of protection. Among the different protocols analysed, the best protocol provided a mean reduction of approximately 52% in the size of the lesion and a reduction of approximately 99% in the parasite load, when the animals received an initial dose of the purified soluble protein P36 of *L. infantum*, followed by a booster with VVp36IL12. In another immunisation protocol, 47% protection was achieved when the initial dose was VVp36IL12 and it was followed by a booster of the purified protein P36 but in this protocol (VVp36IL12+P36), lower type Th1 immunological responses were obtained than in the inverse combination (P36+VVp36IL12). The expression of IL-12 was important to achieve higher levels of protection, since the other protocols that implied the initial administration of soluble P36 and the booster with VVp36 were less efficacious in protecting than when IL-12 was co-expressed with the antigen. Generally, greater reduction in the size of the lesion and the parasite load has been observed when the animals are boosted with VVp36IL12. The inventors, interestingly, noticed no protective effect when the cytosine IL-12 was administered unspecifically twice (immunisations with VVenvIL12). However, other authors have described that with the simple administration of IL-12 supplied by an recombinant adenovirus to susceptible mice, it is possible to protect the animals from fatal mice from fatal leishmaniasis (63). Although not wishing to be linked with any theory or hypothesis, the inventors believe that this beneficial effect is due to the moment of administering the cytosine, administered on the same day as infection with *L. major*. However, in the tests performed in relation to this invention, IL-12 was administered 5 and/or 3 weeks before exposure to the parasite and no protective effect was observed.

It must be emphasised that immunisation with live VV does not exacerbate the infection with *L. major*, as the group of animals that received VVenvIL12 developed a level of infection equal to or slightly less than the group of animals that was not immunised(control group with PBS).

The inventors have previously described (37) that the IL-12 expressed from rVV acts on the elimination of the virus within the host. This is an important observation, since it indicates that the elimination of the vector does not interfere with the ability of the immunogen to induce a powerful immune response against the recombinant antigen. In the same fashion, the use of a live VV that is eliminated is desirable to solve the problems of the virus multiplying with the subsequent activation of specific immune responses against the vector.

To understand better the correlation of the conferred protection with the immune responses, the cellular and humoral immune responses have been characterised before and after exposure to the promastigotes, measuring the relation of IgG2a/IgG1 and IFN-γ/IL-10. Using these parameters, It has been possible to demonstrate that protection was correlated with the activation of an immune response of type Th1. The best protected animals in this study (with smaller sizes of lesions and lower parasitic loads) were those animals that showed the lowest levels of specific IL-10 and IgG1 IL-10, whereas they maintained the highest levels of specific IFN-γ and IgG2a (see tables 1 and 2). This is in accordance with the observations made by other groups in which a type of Th1 immune response is needed to control *Leishmania* infection (10, 11). Thus, the combination of the initial dose with P36 and the booster with VVp36IL12 is an efficacious immunisation protocol against *Leishmania.*

As is known, the presentation of purified proteins to the immune system sets off preferentially a Th2 response. It has also been demonstrated that animals immunised with the protein P36 of *L. major* plus soluble IL-12 were not able to maintain $CD8^+$ cells producing IFN-γ for two weeks, whereas animals immunised with DNA that expressed the same antigen could detect specific $CD8^+$ T cells up to 12 weeks after vaccination. These studies concluded that the proteic antigens administered together with IL-12 are only efficacious in generating a short-term immune response. To induce a more long-lasting protective effect, the use of other vectors is needed (64) In view of these findings, it is believed that after initial dosage with P36, there is an activation of the sub-series of $CD4^+$ and $CD8^+$ T cells, but that after boosting with VVp36IL12 there is an expansion of prepared $CD8^+$ T cells that recognise the target cells infected with the parasite. Although the number of $CD8^+$ T cells activated by this immunisation protocol cannot be determined in the absence of epitopes of P36 of known $CD8^+$ T cells, by comparison with the model of murine malaria in which a well defined epitope of the protein CS (65, 66) has been characterised in great detail, it appears clear that significant numbers of specific memory and effecting $CD8^+$ T cells have to be activated to destroy the cells presenting the antigens of *Leishmania*. Also the contribution of the expressing of NOS induced by IFN-γ in the macrophages in turn inhibits the replication of the parasites. Considering that the inoculum used in this study is quite large, of 500,000 promastigotes (Tests II-IV), whereas in the natural infection, with only one bite of the fly several hundreds of promastigotes are liberated (5). The fact that the immunisation protocol provided by this invention reduces the parasite load by approximately 99% suggests that infection by fly bite will not be achieved in a host with the immune parameters show by the vaccinated animals of this description. Due to the technical limitations of the test used in the development of this invention, which requires a high dose of parasites to evaluate the infection, the inventors cannot guarantee that this immunisation protocol completely eliminates the infection in immunised animals but it will probably reduce the seriousness and the progression of the disease, i.e. it will produce, at least, partial immunity to the immunised animal.

In other models of animal pathogens, it has been demonstrated that rVV administered in a booster dose increases the specific cell immune response against the env. protein of HIV (39), the epitope CS of *Plasmodium yoelii* (66) or the epitope CS of *Plasmodium berghei* (67). It has been shown that the procedure of initial dose-booster can improve the efficacy of the induced response especially when different vectors are used (6669). The protocol of initial dose/booster was most efficacious when rVV was supplied in the booster dose, whereas that for the initial dose could use independently different vectors (66, 67). It has also been shown that the booster with a very attenuated MVA greatly increases the levels of specific $CD8^+$ T cells for HIV-1 in a combination of an initial/booster dose of vectors, ensuring the safety of the immunisation procedure (70).

In the murine model of *Leishmania*, significant protection against infection by *L. major* has been obtained when the animals were administered purified P36 followed by a booster with an rVV that co-expressed P36 and IL-12 (VVp36IL12). This protective effect indicates that the cytosine provides a means to improve the specific immune response to P36 of *Leishmania*. The relevance of the immune protocol provided by this invention is heightened by a combination of initial-booster dose of gp120 of the subunit of HIV-1 and the recombinant canary poxvirus is evaluated in human tests of Phase 1/2 against HIV-1 (71). In the current system, the attenuation of the viral vector is guaranteed by the expression of the cytosine IL-12, as it has been previously demonstrated that the expression of IL-12 of rVV attenuates the vector and allows significant cellular immune response against an antigen such as env of HIV-1 (37).

In conclusion, the VVp36IL12 and the immunisation protocol provided by this invention, which comprises the use of the said rVV, induces an immune response of the type Th1 in mice that produces protection against leishmaniasis. This protocol, in combination with other antigens of *Leishmania*, could have greater application in controlling this and other parasite diseases. The use of very attenuated VV, e.g., MVA ensures safety in human beings.

Micro-Organism Store

A culture of the bacterium derived from *Escherichia coli* carrier of a plasmid that contains the gene that codifies the protein P36 of *L. infantum*, identified as tCI-neo-36, has been deposited in the Colección Española de Cultivos Tipo (CECT), Universidad de Valencia, Edificio de Investigación, Campus de Burjasot, 46100—Burjassot, Valencia, Spain, on Oct. 15, 2000, corresponding to deposit number CECT 5351.

BIBLIOGRAPHY

1. Ashford, R. W., W. Desjeux, and P. de Raadt. 1992. Estimation of population at risk of infection and number of cases of leishmaniasis. *Parasit. Today.* 3(8): 104.
2. World Health Organisation. 1990. Control of leishmaniasis. Expert Comitee. *W.H.O. Tech. Rep. Ser.* 793: 27. Geneve.
3. Beffiffi, S. and L. Gradoni. 1986. Canine leishmaniasis in the Mediterranean area and its implications for human leishmaniasis. *Insect Sci. Applications.* 7: 241.
4. World Health Organisation. 1995. Report on the consultative meeting on *Leishmania* HIV-coinfection. WHO/LEISH/95:1-14. Geneve.
5. Molyneux, D. H. and R. W. Ashford. 1983. The biology of Trypanosoma and *Leishmania*. Taylor and Francis, eds. London.
6. Liew, F. Y. and C. A. O'Donnell. 1993. Immunology of leishmaniasis. *Advanc. Parasit.* 32: 161.
7. Mossman T. R., H. M. Cherwinsky, M. W. Bond, M. A. Gieldin and R. L. Coffman. 1986. Two types of mouse helper T cell clones 1. Definition according to profiles of lymphokine activities and secrete proteins. *J. Immunol.* 136: 2348.
8. S. Romagnani, S. 1991. Human Th1 and Th2 subsets: doubt no more. *Immunol. Today.* 12: 256.
9. Zurawski. G. and J. E. De Vries. 1994. IL-13, an IL4-like cytokine that acts on monocytes and B cells, but not on T cells. *Immunol. Today.* 15: 19.
10. Locksley, R. M., F. P. Heinzel, M. D. Sadick, B. J. Holaday and K. D. Gardner, Jr. 1987. Murine cutaneous leishmaniasis: susceptibility correlates with differential expansion of helper T-cell subsets. *Ann. Inst. Pasteur Immunol.* 138: 744.
11. Sadick, M. D., F. P. Heinzel, B. J. Holaday, R. T. Pu, R. S. Dawkins and R. M. Locksley. 1990. Cure of murine leishmaniasis with anti-interleukin 4 monoclonal antibody. Evidence for a T cell-dependent, interferon gamma-independent mechanism. *J. Exp. Med.* 171: 115.
12. Sacks, D., S. L. Lal, S. N. Shrivastava, J. Blackwell and F. A. Neva. 1997. An analysis of T cell responsiveness in Indian Kala-azar. *J. Immunol.* 138: 908.
13. Ghalib. H. W., J. A. Whittle, M. Kubin, F. A. Hashim, A. M. Elhassan, K. H. Grabstein, G. Trichieri and S. G. Reed. 1995. IL-12 enhances Thl-type responses in human *Leishmania donovani* infections. *J. Immunol.* 154: 4623.
14. Pinelli, E., R. Killick-Kendrick, J. Wagenaar, W. Bemadina, G. del Real and J. Ruitenberg. 1994. Cellular and humoral immune responses in dogs experimentally and naturally infected with *Leishmania infantum*. Infect Immun. 62: 229.
15. Pinelli, E., R. M. Gonzalo, C. J. Boog, V. P. Rutten, D. Gebhard, G. del Real and E. J. Ruitenberg. 1995. *Leishmania infantum* specific T cell lines derived from asymptomatic dogs that lyse infected macrophages in a major histocompatibility complex-restricted manner. *Eur. J. Immunol.* 25: 1594.
16. Mattner F., K. Di Padoya and G. Alber. 1997. Interleukin-12 is indispensable for protective immunity against *L. major. Infect. Immun.* 65: 4378.
17. Trinchieri, G. 1995. Interleukin 12: a proinflammatory cytokine with immunoregulatory functions that bridge innate resistance and antigen-specific adaptive immunity. *Annu. Rev. Immunol* 13: 251.
18. Russell, D. and J. Alexander. 1988. Effective immunization against cutaneous leishmaniasis with defined membrane-antigens reconstituted into liposomes. *J. Immunol.* 140:1274.
19. Champsi, J. and D. McMahon *Pratt.* 1988. Membrane glycoprotein M-2 protects against *L. amazonensis* infection. *Infect. Immun.* 56: 3272.
20. Skeiky, Y. A., J. A. Guderain, D. R. Benson, O. Bacciar, E. M. Carvalho, M. Kubin, R. Baradó, G Trichieru and S. G. Reed. 1995. A recombinant *Leishmania* antigen that stimulates human peripheral blood mononuclear cells to express a Th1-type cytokine profile and produce interleukin-12. *J. Exp. Med.* 181:1527.
21. Skeiky, Y. A., M. Kennedy, D. Kaufman, M. M. Borges, J. A. Guderian, A. Campos-Neto and S. G. Reed. 1998. LeIF: a recombinant *Leishmania* protein that induces IL-12 mediated Th1 cytokine profile. *J. Immunol.* 161: 617.
22. Mougneau, E., F. Altare, A. E. Wakil, S. Zheng, T. Copola, Z. Wang, R. Waldmann, R. Locksley and N. Glaichenhaus. 1995. Expression cloning of a protective *Leishmania* antigen. *Science.* 268:563.
23. Piedrafita, D., D. Xu, D. Hunter, R. A. Haffison and F. Y. Liew. 1999. Protective immune responses induced by vaccination with an expression genomic library of *Leishmania major J. Immunol.* 163: 1467.
24. McMahon-Praft, D., D. Rodriguez, J. R. Rodriguez, Y. Zhang, K. Manson, C. Bergman, L. Rivas, J. F. Rodriguez, K. Lohman, N. Ruddle and M. Esteban. 1993. Recombinant Vaccinia viruses expressing GP46/M2 protect against *Leishmania* infection. Infect. Immu. 61: 3351.
25. Mountford, A. P., S. Anderson and R. A. Wilson, 1996. Induction of Th1 cell-mediated protective immunity to *Schistosoma mansoni* by co-administration of larvas antigens and IL-12 as an adjuvant. J. Immunol. 156: 4739.
26. Miller, M. A., M. J. Skeen and H. K. Ziegler. 1995. Nonviable bacterial antigens administered with IL-12 generate antigen-specific T cell responses and protective immunity against *Listeria monocytogenes. J. Immunol.* 155: 4817.
27. Mahon B. P., M. S. Ryan, F. Griffinn and K. H. G. Mills. 1996. Interleukin 12 produced by macrophages in response to live or killed *Bordetella pertusis* and enhances the efficacy of an acellular Pertusis vaccine by promoting induction of Th1 cells. *Infect. Immun.* 64: 5295.
28. Gurunathan, S., D. L. Sacks, D. R. Brown, S. L. Reiner, H. Charest, N. Glaichenhaus and R. A. Seder. 1997. Vaccination with DNA encoding the immunodominant LACK parasite antigen confers protective immurity to mice infected with *Leishmania major J. Exp. Med.* 186:1137.
29. González-Aseguinolaza, G., S. Taladriz, A. Marquet and V. Larraga. 1999. Molecular cloning, cell localization and 29. binding affinity to DNA replication proteins of the p36/LACK protective antigen from *Leishmania infantum. Eur. J. Biochem.* 259: 909.

30. Taladriz, S., G. Gonzáclez-Aseguionolaza, A. Marquet and V. Larraga. 1999. Cloning, molecular analysis and differential cell localisation of the p36 RACK analogue antigen from the parasite protozoon *Crithidia fasciculata*. FEBS Lett. 443: 375.
31. WHO 1980. The Global Eradication of Smallpox: Final report of the global commission for the certification of smallpox eradication. History of International Public Health. No. 4. World Wealth Organisation. Geneve.
32. Moss, B. 1991. Vaccinia virus: a tool for research and vaccine development. *Science.* 252: 1662.
33. Taylor, J., R. Weinberg, J. Tartaglia, C. Richardson, G. Alkhatib, D. Briedis, M. Appel, E. Norton and E. Paoletti. 1992. Nonreplicating viral vectors as potential vaccines: recombinant canarypox virus expressing measles virus fusion (F) and hemagglutinin (HA) glycoproteins. *Virology.* 187: 321.
34. Paoletti, E. 1996. Applications of pox virus vectors to vaccination: an update. *Proc. Natl. Acad. Sci. U.S.A.* 93: 11349.
35. Kieny, M. P., R. Lathe, R. Drillien, D. Spehner, D. Skory, Schmitt T. Wiktor, H. Koprowski and J. P. Lecocq. 1984. Expression of rabies virus glycoprotein from a recombinant Vaccinia virus. *Nature.* 312: 163.
36. Sutter, G. 1994. A recombinant vector derived from the host range restricted and highly attenuated MVA strain of vaccinia virus stimulates protective immunity in mice to influenza virus. *Vaccine.* 12: 1032.
37. Gherardi, M. M., J. C. Ramirez, D. Rodriguez, J. R. Rodríguez, G. Sano, F. Zavala and M. Esteban. 1999. IL-12 delivery from recombinant Vaccinia virus attenuates the vector and enhances the cellular immune response against HIV-1 env in a dose-dependent manner. *J. Immunol.* 162: 6724.
38. Chakrabarti, S., K. Brechling and B. Moss. 1985. Vaccinia virus expression vector: coexpression of beta-galactosidase provides visual screening of recombinant virus plaques. *Mol. Cell. Biol.* 5: 3403.
39. Chakrabarti, S., J. R. Sisler and B. Moss. 1997. Compact, synthetic, Vaccinia virus early/late promoter for protein expression. *Biotechniques.* 23: 1094.
40. Carroll, M. W. and B. Moss. 1995. *E. coli* beta-glucuronidase (GUS) as a marker for recombinant vaccinia viruses. Biotechniques. 19: 352.
41. Dallo, S. and M. Esteban. 1987. Isolation and characterization of attenuated mutants of vaccinia virus. *Virology.* 159: 408.
42. Hogan, S. P., P. S. Foster, X. Tan and A. J. Ramsay. 1998. Mucosal IL-12 gene delivery inhibits allergic airways disease and restores local activiral immunity. *Eur. J. Immunol.* 28:413.
43. Buffet P. A., A. Sulahian, Y. J. Garin, N. Nassar, and F. Derouin. 1995. Culture microtitration: a sensitive method for quantifying-*Leishmania infantum* in tissues of infected mice. *Antimicrob. Agents Chemother.* 39: 2167.
44. Sypek, J. P., C. L. Chung, S. E. H. Mayor, S. J. Subramanyam, S. J. Goldman, D. S. Sieburth, S. F. Wolf, and R. G. Schaub. 1993. Resolution of cutaneous leishmaniasis: interleukin 12 initiates a protective T helper type 1 immune response. *J. Exp. Med.* 177:1793.
45. Bliss J., V. Van Cleave, K. Murray, A. Wiencis, M. Ketchum, R. Maylor, T. Haire, C. Resmini, A. K. Abbas and S. F. Wolf. 1996. IL-12, as adjuvant, promotes a T helper 1 cell, but not suppress a T helper 2 recall response. *J. Immunol.* 156: 887.
46. Trinchieri, G. 1998. Immunobiology of interleukin-12. *Immunol. Res.* 17: 269.
47. Heinzel, F. P., M. D. Sadick, B. J. Holaday, R. L. Coffman and R. M. Locksley. 1989. Reciprocal expression of interferon gamma or interleukin 4 during the resolution or progression of murine leishmaniasis. Evidence for the expansion of distinct helper T cell subsets. *J. Exp. Med.* 169: 59.
48. Boom W. H., L. Liebster, A. K. Abbas and R. G. Titus. 1990. Patterns of cytokine secretion in murine leishmaniasis: correlation with disease progression or resolution. *Infect. Immun.* 58: 3863.
49. Heinzel, F. P., M. D. Sadick, S. S. Mutha and R. M. Locksley. 1991. Production of interferon gamma, interleukin 2 and interleukin 10 by $CD4^+$ lymphocytes in vivo during healing and progressive murine leishmaniasis. *Proc. Natl. Acad. Sci. USA.* 88: 7011.
50. Heinzel, F. P., D. S. Schoenhaut, R. M. Rerko, L. E. Rosser and M. K. Gately. 1993. Recombinant interleukin 12 cures mice infected with *Leishmania major. J. Exp. Med.* 177: 1505.
51. Sypek, J. P., C. L. Chung, S. E. H. Mayor, S. J. Subramanyam, S. J. Goldman, D. S. Sichurth, S. F. Wolf, and R. G. Schaub. 1993. Resolution of cutaneous leishmaniasis: interleukin 12 initiates a protective T helper type 1 immune response. *J. Exp. Med.* 177: 1793.
52. Finkelman, F. D., J. Holmes and I. M. Katona. 1990. Lymphokine control of in vivo immunoglobulin isotype selection. *Annu. Rev. Immunol.* 158: 816.
53. Bodgan, C., K. Schhroppel, M. Lohoff, M. Rollinghoff and W. Solbach. 1990. Immunization of susceptible hosts with a soluble antigen fraction from *L. major* leads to aggravation of murine leishmaniasis mediated by CD4+ T cells. *Eur. J. Immunol.* 20: 2533.
54. Wei, X-Q., I. G. Charles, A. Smith, J. Ure, G.-J-Feng, F.-P. Huang, D. Xu, W. Muller, S. Moncada and F. Y. Liew. 1995. Altered immune responses in mice lacking inducible nitric oxide synthase. *Nature.* 375: 408.
55. Noben-Trauth, N., P. Kropf and I. Müller. 1996. Susceptibility to *Leishmania major* infection in interleukin-4 deficient mice. *Science.* 271: 987.
56. Kaye, P. M., C. Coburn, M. McCrossan and S. M. Beverly. 1993. Antigens targeted to the *Leishmania* phagolysosome are processed for CD4+ T cell recognition. *Eur. J. Immunol.* 23: 2311.
57. Nacy, C. A., B. J. Nelson, M. S. and S. J. Green. 1991. Cytokines that regulate macrophage production of nitrogen oxides and expression of anti-leishmanial activities. *Res. Immunol.* 144: 268.
58. Green, S. J., C. A. Nacy and M. S. Meltzer. 1991. Cytokine-induced synthesis of nitrogen oxides in macrophages: a protective host response to *Leishmania* and other intracellular pathogens. *J. Luekoc.* 50: 93.
59. Green, S. J., R. M. Crawford, J. T. Hockmeyer, M. S. Meltzer and C. A. Nacy. 1990. *Leishmania major* amastigotes initiate the L-arginine-dependant killing mechanism in IFN-gamma-stimulated macrophages by induction of tumor necrosis factor-alpha. *J. Immunol.* 145: 4290.
60. Liew F. Y., Y. Li and S. Millot. 1990. Tumor necrosis factor-α sinergises with IFN-γ in mediating killing of *Leishmania major* through the induction of nitric oxide. *J. Immunol.* 145: 4306.
61. Cox F. E. G. 1997. Designer vaccines for parasitic diseases. *Intl. J. Parasitol.* 27: 147.

62. Afonso, L. C. C., T. Scharton, L. Q. Viera, M. Wysocka, G. Trichieri and P. Scott 1994. The adjuvant effect of interleukin-12 in a vaccine against *Leishmania major Science.* 263: 235.
63. Gabaglia, C. R., B. Pedersen, M. Hitt, N. Burdin, E. Sercarz, F. Graham, J. Gauldie and T. Braciak. 1999. A single intramuscular injection with Adenovirus-expressing IL-12 protects Balb/c mice against *Leishmania major* infection, while treatment with IL-4-expressing vector increases disease susceptibility in B10D2 mice. *J. Immunol.* 162: 753.
64. Gurunathan, S., C. Prussin, D. L. Sacks and R. A. Seder. 1998. Vaccine requirements for sustained cellular immunity to an intracellular parasitic infection. *Nature Med.* 4: 1409.
65. Rodrigues, M. M., A-S. Cordey, G. Arreaza, G. Corradin, P. Romero, J. L. Maryanski, R. S. Nussenzweig and F. Zavala. 1991. CD8+ cytolitic T cell clones derived against the *Plasmodium yoelii* circumsporozoite protein protects against malaria. *Int. Immunol.* 3: 579.
66. Miyahira, Y., A. García-Sastre, D. Rodriguez, J. R. Rodriguez, K. Murata, M. Tsuji, P. Palese, M. Esteban, F. Zavala and R. S. Nussenzzweig. 1998. Recombinant viruses expressing a human malaria antigen elicit protective immune CD8+ T cell responses in mice. *Proc. Natl. Acad. Sci. USA.* 95: 3954.
67. Schneider, J., S. C. Gilbert, C. M Hannan, P. Dégano, E. Prieur, E. G. Sheu, M. Plebanski and A. Y. S. Hill. 1999. Induction of CD8+ T cells using heterologous prime-boost immunisation strategies. *Immunol. Rev.* 170: 29.
68. Sedegah M., T. R. Jones, M. Kaur, R. Hedstrom, P. Hobart, J. A. Tine and S. L. Hoffmnan. 1998. Boosting with recombinant Vaccinia increases immunogenicity and protective efficacy of malaria DNA vaccine. *Proc. Natl. Acad. Sci.* 95: 7648.
69. Gonzalo, R. M., D. Rodriguez, A. García-Sastre, J. R. Rodriguez, P. Palese and M. Esteban. 1999. Enhanced CD8+ T cell response to HIV-1 env by combined immunization with Influenza and Vaccinia virus recombinants. *Vaccine.* 17: 887.
70. Hanke, T. and A. McMichael. 1999. Preclinical development of a multi-CTL epitope-based DNA prime MVA boost vaccine for AIDS. *Immunol. Lett.* 1-3: 177.
71. Girard, M., A. Habel and C. Chanel. 1999. New prospects for the development of a vaccine against human immunodeficiency virus type 1. An overview. *C. R. Acad. Sci. III.* 11: 959.
72. Bern C., Jha S N, Joshi A B, Thakur G D, Bista M B 2000. Use of the recombinant K39 dipstick test an the direct agglutination test in a setting endemic for visceral leishmaniasis in Nepal. Am J Trop Med Hyg. 63: 1537.

The invention claimed is:

1. A vaccine for protecting an animal from *Leishmania infantum* infection by an immunization protocol which comprises an initial immunization and a booster dose, said vaccine comprising two separate components: (i) soluble *Leishmania infantum* P 36 protein in a therapeutically effective amount, and
    (ii) a non-*Escherichia coli* expression system comprising a DNA sequence encoding the *Leishmania infantum* P36 protein and a DNA sequence encoding interleukin-12, and wherein said expression system provides for the simultaneous expression of said *Leishmania infantum* P36 protein and interleukin-12, and wherein said soluble *Leishmania infantum* P36 protein is administered to said animal as an initial immunization, and said non-*Escherichia coli* expression system comprising the DNA sequence encoding the *Leishmania infantum* P36 protein and the DNA sequence encoding interleukin-12 is administered as as a booster dose.

2. The vaccine of claim 1, in which the non-*Escherichia coli* expression system is a vector selected from the group consisting of a pCI-neo plasmid and a Vaccinia virus, wherein the DNA sequence encoding the *L. infantum* P36 protein and the DNA sequence encoding interleukin-12 are cloned for simultaneous expression of said *L. infantum* P36 protein and interleukin-12.

3. The vaccine of claim 1 further comprising a substance selected from the group consisting of adjuvants and pharmaceutically acceptable vehicles.

4. A method of protecting an animal from *Leishmania infantum* infection, comprising administering to the animal an initial vaccine comprising a first immunogen and a booster vaccine comprising a second immunogen, wherein: (i) the first immunogen comprises a soluble *Leishmania infantum* P36 protein and the second immunogen comprises a non-*Escherichia coli* expression system comprising a DNA sequence encoding said *Leishmania infantum* P36 protein and a DNA sequence encoding interleukin-12, wherein said expression system provides for the simultaneous expression of said P36 protein and interleukin-12.

5. The method of claim 4 wherein the non-*Escherichia coli* expression system is a vector selected from the group consisting of a recombinant pCI-neo plasmid or Vaccinia virus, wherein the DNA sequence encoding the *L. infantum* P36 protein and the DNA sequence encoding interleukin-12 are cloned for simultaneous expression of said *L. infantum* P36 protein and interleukin-12.

6. The method of claim 5 wherein the plasmid or Vaccinia virus further comprises at least a DNA sequence encoding a protein selected from the group consisting of *L. infantum* P36 protein and a DNA sequence encoding for murine interleukin-12, operatively linked to a transcription regulation region.

7. The method of claim 4 wherein the non-*Escherichia coli* expression system is a Vaccinia type expression system.

8. The method of claim 7 wherein the Vaccinia type expression system comprises VVp36.

9. The method of claim 4 wherein the non-*Escherichia coli* expression system is a plasmid type expression system.

10. The method of claim 9 in which the plasmid type expression system comprises pRSET-B.

11. A vaccine for protecting an animal from *Leishmania infantum* infection by an immunization protocol which comprises an initial immunization and a booster dose, wherein said vaccine comprises two separate components: (i) a plasmid which comprises a DNA sequence encoding for *L. infantum* P36 protein, and (ii) a recombinant Vaccinia virus comprising a DNA sequence encoding for *L. infantum* P36 protein, wherein
    said plasmid which comprises a DNA sequence encoding for *L. infantum* P36 protein is administered to said animal as an initial immunization; and
    said recombinant Vaccinia virus comprising a DNA sequence encoding for *L. infantum* P36 protein is administered as a booster dose.

\* \* \* \* \*